(12) United States Patent
Murai et al.

(10) Patent No.: US 8,735,887 B2
(45) Date of Patent: May 27, 2014

(54) ION SENSOR AND DISPLAY DEVICE

(75) Inventors: Atsuhito Murai, Osaka (JP); Yoshiharu Kataoka, Osaka (JP); Takuya Watanabe, Osaka (JP); Yuhko Hisada, Osaka (JP); Satoshi Horiuchi, Osaka (JP)

(73) Assignee: Sharp Kabushiki Kaisha, Osaka (JP)

( * ) Notice: Subject to any disclaimer, the term of this patent is extended or adjusted under 35 U.S.C. 154(b) by 0 days.

(21) Appl. No.: 13/701,112

(22) PCT Filed: May 18, 2011

(86) PCT No.: PCT/JP2011/061380
§ 371 (c)(1),
(2), (4) Date: Dec. 11, 2012

(87) PCT Pub. No.: WO2011/152209
PCT Pub. Date: Dec. 8, 2011

(65) Prior Publication Data
US 2013/0313554 A1   Nov. 28, 2013

(30) Foreign Application Priority Data
Jun. 3, 2010   (JP) .................................. 2010-128168

(51) Int. Cl.
*G01N 27/414*   (2006.01)
(52) U.S. Cl.
USPC .............................. 257/53; 257/71; 257/253
(58) Field of Classification Search
USPC ......... 257/57, 59, 72, 83, 257, 290, 351, 368, 257/392
See application file for complete search history.

(56) References Cited

U.S. PATENT DOCUMENTS

| 4,056,772 | A | 11/1977 | Graf von Berckheim |
| 4,061,476 | A | 12/1977 | Hölter et al. |
| 4,123,502 | A | 10/1978 | Hölter et al. |
| 4,201,751 | A | 5/1980 | Holter et al. |
| 4,206,186 | A | 6/1980 | Hölter et al. |
| 2002/0117694 | A1* | 8/2002 | Migliorato et al. ........... 257/253 |
| 2002/0158645 | A1* | 10/2002 | Chou et al. .................... 324/760 |
| 2005/0062093 | A1* | 3/2005 | Sawada et al. ................ 257/316 |
| 2006/0035400 | A1* | 2/2006 | Wu et al. ....................... 257/253 |
| 2007/0229087 | A1* | 10/2007 | Okano .......................... 324/464 |

FOREIGN PATENT DOCUMENTS

| JP | 51-113692 A | 10/1976 |
| JP | 10-332164 A | 12/1998 |
| JP | 2002-296229 A | 10/2002 |
| JP | 2003-336872 A | 11/2003 |
| JP | 2004-156855 A | 6/2004 |
| JP | 2008-215974 A | 9/2008 |

OTHER PUBLICATIONS

Official Communication issued in International Patent Application No. PCT/JP2011/061380, mailed on Jun. 14, 2011.

(Continued)

*Primary Examiner* — Marcos D. Pizarro
*Assistant Examiner* — Quinton Brasfield
(74) *Attorney, Agent, or Firm* — Keating & Bennett, LLP

(57) ABSTRACT

The present invention provides an ion sensor with which an ion concentration can be stably measured with high accuracy, and a display device. The present invention is an ion sensor that includes a field effect transistor. The ion sensor also includes an ion sensor antenna and a reset device. The ion sensor antenna and the reset device are connected to a gate electrode of the field effect transistor. The reset device is capable of controlling the potential of the gate electrode and the ion sensor antenna to a predetermined potential.

7 Claims, 20 Drawing Sheets

(56) References Cited

OTHER PUBLICATIONS

Murai et al, "Display Device", U.S. Appl. No. 13/701,117, filed Nov. 30, 2012.

Murai et al, "Ion Sensor and Display Device", U.S. Appl. No. 13/701,123, filed Nov. 30, 2012.

Murai et al, "Ion Sensor, Display Device, Method for Driving Ion Sensor, and Method for Calculating Ion Concentration", U.S. Appl. No. 13/701,129, filed Nov. 30, 2012.

* cited by examiner

ION SENSOR AND DISPLAY DEVICE

TECHNICAL FIELD

The present invention relates to an ion sensor and a display device. More specifically, the present invention relates to an ion sensor which measures the ion concentration with high precision and is suitable for use in devices such as an ion generator; and a display device provided with the ion sensor.

BACKGROUND ART

A technology of generating positive ions and negative ions (hereinafter, also referred to as "both ions" or simply as "ions") in the air has recently been found to have an effect of killing bacteria floating in the air and purify the air. An ion generator employing the technology, such as an air purifier, has matched the comfort and the recent trends towards health-conscious lifestyle, and thus has drawn much attention.

Since ions are invisible, checking generation of ions by direct eye-observation is not possible. Still, users of devices such as air purifiers naturally want to know if ions are successfully generated and if the ions generated have a desired concentration.

In this respect, Patent Literature 1, for example, discloses an air conditioner or air purifier provided with an ion sensor for measuring the ion concentration in the air, and a display for displaying the ion concentration measured with the ion sensor.

An ion sensor of course is preferred to have high precision for precise measurement of the concentration of ions produced in the air.

In this respect, the following sensors are available. Patent Literature 2, for example, discloses a biosensor that changes the voltage to be applied to the back gate to adjust the electric potential of the gate electrode and suppress variation in threshold. Patent Literature 3, for example, discloses a field effect transistor ion sensor which includes a field effect transistor and an ion sensor integrally formed, and reduces the influence of measurement environment.

Also known is an ion generating element provided with an ion sensor portion for determining the amounts of positive ions and negative ions generated from the ion generating portion and a display for displaying the amounts of ions determined as described in, for example, Patent Literature 4. Furthermore, a remote control for electric appliances with a built-in ion sensor is known which is provided with an ion sensor for measuring the ion concentration in the air and a display for displaying the current state of the electric appliances, as described in, for example, Patent Literature 5.

CITATION LIST

Patent Literature

Patent Literature 1: JP H10-332164 A
Patent Literature 2: JP 2002-296229 A
Patent Literature 3: JP 2008-215974 A
Patent Literature 4: JP 2003-336872 A
Patent Literature 5: JP 2004-156855 A

SUMMARY OF INVENTION

Technical Problem

However, the conventional ion sensors described in Patent Literatures 1 to 3 are susceptible to the influence of external noise such as electrostatic charges or electrical noise, and the operations of the sensors are unstable. Therefore, it is difficult for such sensors to stably measure an ion concentration with high accuracy.

The present invention has been made in view of the above described present situation, and an object of the present invention is to provide an ion sensor with which an ion concentration can be stably measured with high accuracy, and a display device.

Solution to Problem

The inventors conducted various studies regarding ion sensors with which an ion concentration can be stably measured with high accuracy, and focused attention on ion sensor antennas that are conductive members that detect (capture) ions in air. The inventors found that in the conventional ion sensors, an ion sensor antenna is in an electrically floating state, and therefore the conventional ion sensors are susceptible to the influence of external noise such as electrostatic charges or electrical noise and the operations of the sensors are unstable. Consequently, the sensors can not stably measure an ion concentration with high accuracy. Further, the inventors found that by providing a reset device that is connected to an ion sensor antenna and a gate electrode of a field effect transistor, and controlling a potential of the gate electrode and the ion sensor antenna to a predetermined potential by means of the reset device, the potential of the gate electrode of the field effect transistor and the ion sensor antenna can be reset to a predetermined potential, that is, calibrated, before performing measurement of an ion concentration. Having realized that this idea can beautifully solve the above problem, the inventors have arrived at the present invention.

More specifically, one aspect of the present invention provides an ion sensor that includes a field effect transistor, the ion sensor further including an ion sensor antenna and a reset device, wherein the ion sensor antenna and the reset device are connected to a gate electrode of the field effect transistor, and the reset device is capable of controlling a potential of the gate electrode and the ion sensor antenna to a predetermined potential.

The ion sensor is described in detail hereinafter.

The ion sensor includes a field effect transistor (hereinafter, also referred to as an "FET"). The electrical resistance of the channel of the FET changes depending on the detected concentration of ions. The ion sensor detects the change as a current or voltage change between the source and drain of the FET.

The FET may be of any kind, but is preferably a thin film transistor (hereinafter, also referred to as a "TFT") or a metal oxide semiconductor FET (MOSFET). A TFT is suitable for an active-matrix driven liquid crystal display device or an organic electro-luminescence (organic EL) display device. A MOSFET is suitable for a semiconductor chip for components such as LSIs and ICs.

Any semiconductor material may be used for TFTs. Examples of the material include amorphous silicon (a-Si), polysilicon (p-Si), microcrystalline silicon (μc-Si), continuous grain silicon (CG-Si), and oxide semiconductors. Any semiconductor material may be used for MOSFETs. Examples of the material include silicon.

The ion sensor further includes an ion sensor antenna (hereinafter also simply referred to as an "antenna") which is connected to the gate electrode of the field effect transistor. The antenna is a conductive component that detects (captures) ions in the air. More specifically, ions reaching the antenna charge the surface of the antenna, which leads to an electric potential change of the gate electrode of the FET that is connected to the antenna. The change results in a change in the electrical resistance of the channel of the FET.

The ion sensor further includes a reset device, and the reset device is connected to a gate electrode of the field effect transistor and can control a potential of the gate electrode and the ion sensor antenna to a predetermined potential. Thus, measurement of an ion concentration can be started after the potential of the gate electrode of the FET and the antenna is reset to a predetermined potential, that is, calibrated. Accordingly, an ion sensor can be realized that is highly resistant to the influence of external noise such as electrostatic charges or electrical noise, in which sensor operations are stable, and which provides high measurement accuracy.

The ion sensor including these components as its essential components is not particularly limited by other components.

In the following, a preferable embodiment of the ion sensor is described in detail.

Preferably the reset device includes a switching element, and after applying a predetermined voltage to the gate electrode and the ion sensor antenna, the reset device places the gate electrode and the ion sensor antenna in a high impedance state. Therefore, after the gate electrode of the FET and the antenna are controlled to a predetermined potential by the reset device, the gate electrode and antenna can be placed in a high impedance state during measurement of an ion concentration. Thus, unwanted variations in the potential of the gate electrode of the FET and the antenna by means of the reset device during measurement of an ion concentration can be suppressed. That is, the sensor operations can be made more stable and the accuracy can be further increased.

Note that, although the switching element is not particularly limited, the switching element is suitably an FET, and a TFT and a MOSFET are more suitable.

Preferably the ion sensor further includes a capacitor, wherein one terminal of the capacitor is connected to the gate electrode and the ion sensor antenna, and the other terminal of the capacitor is set to a predetermined potential. Since it is thereby possible to increase the capacitance of the gate electrode and the ion sensor antenna, the influence of external noise during measurement of an ion concentration can be suppressed. Accordingly, the sensor operations can be made more stable and the accuracy can be further increased.

Thus, another aspect of the present invention provides an ion sensor including a field effect transistor, the ion sensor further including an ion sensor antenna and a capacitor, wherein the ion sensor antenna and one terminal of the capacitor are connected to a gate electrode of the field effect transistor, and the other terminal of the capacitor is set to a predetermined potential.

Preferably the FET includes amorphous silicon or microcrystalline silicon. By using the comparatively inexpensive a-Si or μc-Si, it is possible to provide an ion sensor that has high accuracy while also having a low manufacturing cost.

The gate electrode may be a first gate electrode, and the field effect transistor may also have a second gate electrode. Thus, the first gate electrode can be configured to function as a back-gate electrode, and the second gate electrode configured to function as a gate electrode main body. Accordingly, it is possible to measure a concentration of both positive ions and negative ions with a single FET.

On the other hand, the field effect transistor need not have a gate electrode other than the gate electrode. It is thus possible to improve the sensitivity of the sensor in comparison to a configuration which has a back-gate electrode.

Yet another aspect of the present invention is a display device provided with the ion sensor, a display including a display-driving circuit, and a substrate. The field effect transistor, the ion sensor antenna, and at least one portion of the display-driving circuit are formed on the same main surface of the substrate. Thereby, the ion sensor can be provided in a vacant space (e.g., picture-frame region) of the substrate, and the ion sensor can be formed using the process of forming the display-driving circuit. As a result, a display device can be produced which is provided with the ion sensor and the display, can be produced at a low cost, and can be miniaturized.

The display device may be of any kind, and its suitable examples include flat panel displays (FPDs). Examples of the FPDs include liquid crystal display devices, organic electroluminescence displays, and plasma displays.

The display includes elements for performing the display functions, and includes, for example, display elements and optical films in addition to the display-driving circuit. The display-driving circuit is a circuit for driving the display elements, and includes, for example, circuits such as a TFT array, a gate driver, and a source driver. Particularly, a TFT array is preferably used as the at least one portion of the display-driving circuit.

The display element has a light-emitting function or light-controlling function (shutter function for light), and is provided for each pixel or sub-pixel of the display device.

For example, a liquid crystal display device usually includes a pair of substrates, and has display elements having a light-controlling function between the substrates. More specifically, the display elements of the liquid crystal display device each usually include a pair of electrodes, and liquid crystals placed between the substrates.

An organic electroluminescence display usually has display elements having a light-emitting function on a substrate. More specifically, the display elements of the organic EL display each usually have a structure in which an anode, an organic electroluminescence layer, and a cathode are stacked.

A plasma display usually has a pair of substrates facing each other, and display elements having a light-emitting function which are placed between the substrates. More specifically, the light-emitting elements of the plasma display usually include a pair of electrodes; a fluorescent material formed on one of the substrates; and rare gas enclosed between the substrates.

The display device having the above components as its essential components is not particularly limited by other components.

Preferred embodiments of the display device are described in detail below.

Preferably the reset device is formed inside a semiconductor chip, and the semiconductor chip is mounted on the substrate. Thus, in comparison to a configuration in which the reset device is formed directly on the substrate, the gate electrode and the antenna can be placed in a high impedance state more effectively during measurement of an ion concentration.

The FET is the first FET. The display-driving circuit includes the second FET. The first FET, the ion sensor antenna, and the second FET are preferably formed on the same main surface of the substrate. With these structures, at least part of the materials and processes for forming the first and second FETs can be the same, and thus the cost required for formation of the first and second FETs can be reduced.

A device provided with a conventional ion sensor and a display usually utilizes parallel plate electrodes for the ion sensor. For example, the ion sensor of Patent Literature 4 is provided with a plate-shaped accelerating electrode and a plate-shaped capturing electrode which face each other. Such a parallel plate ion sensor cannot be processed easily on the order of micrometers because of the limit of processing accuracy in production. Hence, miniaturization of the ion sensor is difficult. Also on the remote control for electric appliances with a built-in ion sensor described in Patent Literature 5, a parallel plate electrode, consisting of a pair of an ion-accelerating electrode and an ion-capturing electrode, is provided. Miniaturization of such an ion sensor is also difficult. In contrast, use of an FET and an ion sensor antenna for an ion sensor element as in the above structure allows production of the ion sensor element by photolithography. Thereby, the ion sensor can be processed on the order of micrometers, and therefore can be more miniaturized than the parallel plate ion sensors. The electrode gap (gap between the TFT array substrate and counter substrate) in the liquid crystal display device is usually about 3 to 5 µm. In the case that an electrode is provided to each of the TFT array substrate and the counter substrate such that a parallel plate ion sensor is formed, introduction of ions into the gap is considered difficult. Meanwhile, since the ion sensor element including an FET and an antenna as in the above structure eliminates the need for a counter substrate, the display device provided with the ion sensor can be miniaturized.

The ion sensor element is an element that is minimum required to convert the ion concentration in the air to an electric, physical amount.

Although the kind of the second FET is not particularly limited, a TFT is preferable. Since TFTs are generally used in an FPD such as an organic EL display device or a liquid crystal display device that employs the active matrix driving method, a TFT is suitable for the display device.

The semiconductor material may be any material in the case that the second FET is a TFT. Examples of the semiconductor material include a-Si, µ-Si, CG-Si, and oxide semiconductors. Particularly, a-Si and µc-Si are preferred.

Preferably, the ion sensor antenna has a surface (exposed portion) that includes a transparent conductive film. In other words, preferably the surface of the ion sensor antenna is covered by the transparent conductive film. A transparent conductive film is highly resistant to corrosion, and therefore an unexposed portion (for example, a portion that includes metal lines) of the ion sensor antenna can be prevented from being exposed to the external environment and corroding.

The transparent conductive film is the first transparent conductive film, and the display preferably includes the second transparent conductive film. Since the transparent conductive film has conductivity and optical transparency, the second transparent conductive film can be suitable for use as a transparent electrode of the display. Also, at least part of the materials and processes for the first transparent conductive film and the second transparent conductive film can be the same. Accordingly, the first transparent conductive film can be formed at a low cost.

The first transparent conductive film and the second transparent conductive film preferably contain the same material(s), and more preferably consist only of the same material(s). Such a structure enables to form the first transparent conductive film at a low cost.

The material of each of the first transparent conductive film and the second transparent conductive film may be any material. For example, indium tin oxide (ITO), indium zinc oxide (IZO), zinc oxide (ZnO), and fluorine-doped tin oxide (FTO) are suitable.

The first FET preferably includes a semiconductor whose properties are changed by light, and the semiconductor is preferably shielded from light by a light-shielding film. Examples of the semiconductor whose properties are changed by light include a-Si and µc-Si. In order to use these semiconductors for an ion sensor, the light is preferably blocked such that the properties do not change. Shielding, from light, the semiconductor whose properties are changed by light enables suitable use of the semiconductor not only for a display but also for an ion sensor.

The light-shielding film shields the first FET from light outside the display device (external light) and/or light inside the display device. Examples of the light inside the display device include reflected light produced inside the display device. In the case that the display device is a spontaneous light emission display device such as an organic EL display and a plasma display, examples of the light inside the display device include light emitted from the light-emitting elements provided in the display device. Meanwhile, in the case of a non-spontaneous light emission liquid crystal display device, examples of the light inside the display device include light from the backlight. The reflected light produced inside the display device is about several tens of lux, and the influence on the first FET is comparatively small. Examples of the external light include sunlight and interior illumination (e.g., fluorescent lamp). The sunlight is 3000 to 100000 Lx, and the interior fluorescent lamp at the time of actual use (except for use in a dark room) is 100 to 3000 Lx. Both lights greatly influence the first FET. The light-shielding film preferably shields the first FET from at least the external light, and more preferably blocks both the external light and the light inside the display device.

Preferably, the light-shielding film is the first light-shielding film, and the display has the second light-shielding film. With such a structure, in the case that a liquid crystal display device or an organic EL display is used as the above display device, the second light-shielding film can be provided at borders between the pixels or sub-pixels in the display for prevention of color mixing. Also, at least part of the materials and processes for forming the first light-shielding film and the second light-shielding film can be the same, and therefore the first light-shielding film can be formed at a low cost.

The first light-shielding film and the second light-shielding film preferably contain the same material(s), and more preferably consist only of the same material(s). The first light-shielding film therefore can be formed at a low cost.

The ion sensor antenna may or may not overlap the channel region of the first FET. Since the antenna usually does not include a semiconductor whose properties are changed by light, light shielding is not necessary. That is, in the case that the first FET needs to be shielded from light, a light-shielding film is not necessary around the antenna. Accordingly, provision of an antenna outside the channel region (i.e., the antenna does not overlap the channel region) enables free choice of the antenna arrangement position regardless of the first FET arrangement position. The free choice allows easy formation of an antenna at places where ions can be effectively captured, such as a place near a channel or fan for introducing the air to the antenna. In contrast, provision of an antenna in the channel region (i.e., the antenna overlaps the channel region) allows the gate electrode or back-gate electrode of the first FET itself to function as an antenna. The ion sensor element therefore can be further miniaturized.

At least one portion of the ion sensor and at least one portion of the display-driving circuit are preferably connected to a common power supply. With use of a common power supply, the cost for forming the power supply and the arrangement space for the power supply can be reduced compared to the structure in which the ion sensor and the display have different power supplies. More specifically, at least the source or drain of the first FET and the gates of the TFTs in the TFT array are preferably connected to the common power supply. Also, the reset device and the gates of the TFTs in the TFT array are preferably connected a common power supply.

The display device may be used for any product. Suitable examples of the product include non-portable displays such as displays for televisions and personal computers. To such a non-portable display, the ion concentration in the indoor environment in which the display is placed can be displayed. The suitable examples also include portable devices such as cell phones and personal digital assistants (PDAs). With such a product, the ion concentration at various places can be measured easily. The suitable examples further include ion generators provided with a display. Such an ion generator can show on the display the concentration of ions emitted from the ion generator.

Advantageous Effects of Invention

According to the present invention, it is possible to provide an ion sensor with which an ion concentration can be stably measured with high accuracy, and a display device.

DESCRIPTION OF EMBODIMENTS

The present invention is described in more detail based on the following embodiments, with reference to the drawings. The present invention is not limited to the embodiments.
(Embodiment 1)

Figure 1:
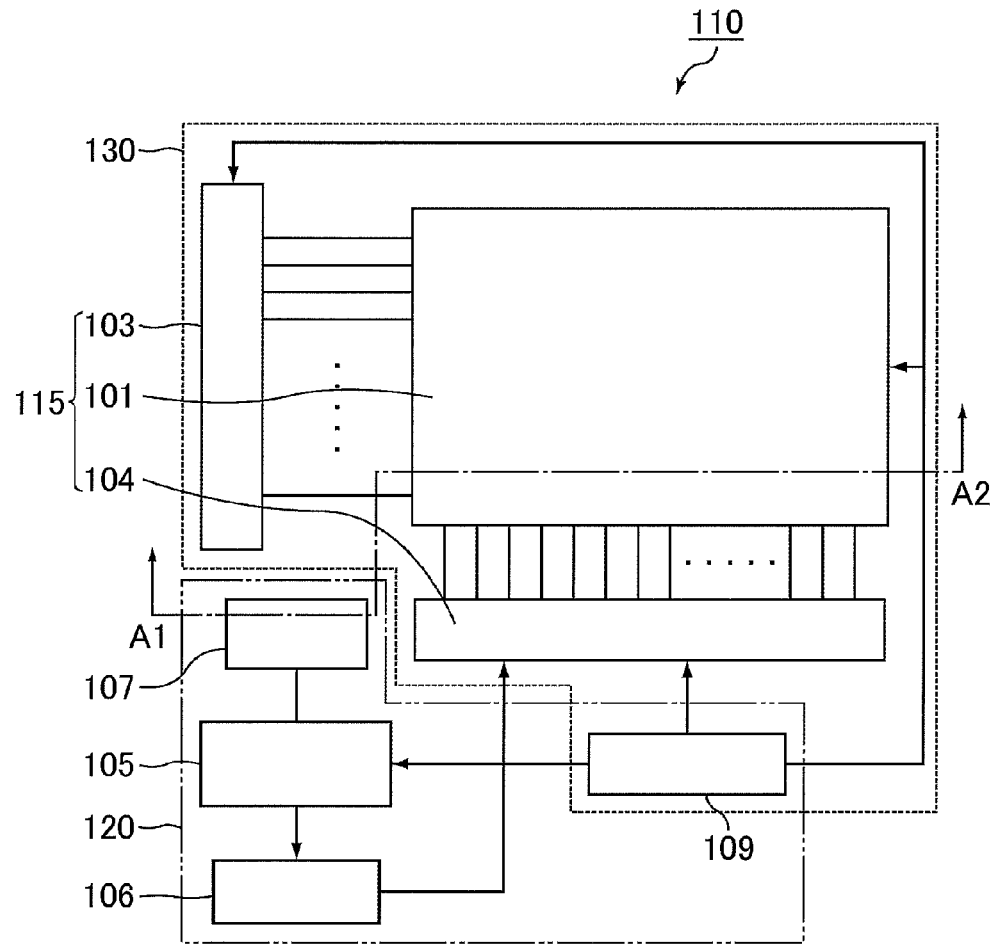
FIG. 1 is a block diagram of an ion sensor and a display device according to Embodiments 1 to 4.

The present embodiment is described taking as an example a liquid crystal display device that is equipped with an ion sensor for which a detection object is negative ions in air. FIG. 1 is a block diagram of an ion sensor and a display device according to the present embodiment.

A display device 110 according to the present embodiment is a liquid crystal display device, and includes an ion sensor 120 (ion sensor portion) for measuring the ion concentration in the air, and a display 130 for displaying various images. The display 130 is provided with a display-driving circuit 115 that includes a display-driving TFT array 101, a gate driver (scanning signal line-driving circuit for display) 103, and a source driver (image signal line-driving circuit for display) 104. The ion sensor 120 includes an ion sensor driving/reading circuit 105, an arithmetic processing LSI 106, and an ion sensor circuit 107. A power supply circuit 109 is shared by the ion sensor 120 and the display 130. The ion sensor circuit 107 is a circuit that includes at least elements (preferably an FET and an ion sensor antenna) required to convert the ion concentration in the air to an electric physical amount, and has a function of detecting (capturing) ions.

The display 130 has the same circuit structure as a conventional active-matrix display device such as a liquid crystal display device. That is, images are displayed in a region with the TFT array 101 formed, i.e., in a display region, by line sequential driving.

An outline of the functions of the ion sensor 120 is as follows. First, the ion sensor circuit 107 detects (captures) negative ions in air, and generates a voltage value that is in accordance with the amount of negative ions that are detected. The voltage value is sent to the driving/reading circuit 105, and is converted into a digital signal by the driving/reading circuit 105. The digital signal is sent to the LSI 106. At the LSI 106, a negative ion concentration is computed based on a predetermined calculation method, and display data for displaying the computation result in a display region is generated. The display data is sent to the TFT array 101 through the source driver 104, and ultimately a negative ion concentration that is in accordance with the display data is displayed. The power supply circuit 109 supplies power to the TFT array 101, the gate driver 103, the source driver 104 and the driving/ reading circuit 105. The driving/reading circuit 105 includes a reset device, and in addition to the above described functions, controls the reset device and supplies a predetermined signal and power to the reset device at a predetermined timing. The driving/reading circuit 105 also supplies predetermined power at a predetermined timing to an input line that is described later.

The driving/reading circuit 105 may be included in another circuit such as the ion sensor circuit 107, the gate driver 103, and the source driver 104, and may be included in the LSI 106.

In the present embodiment, the arithmetic processing may be performed using software that functions on a personal computer (PC) in place of the LSI 106.

Figure 2:
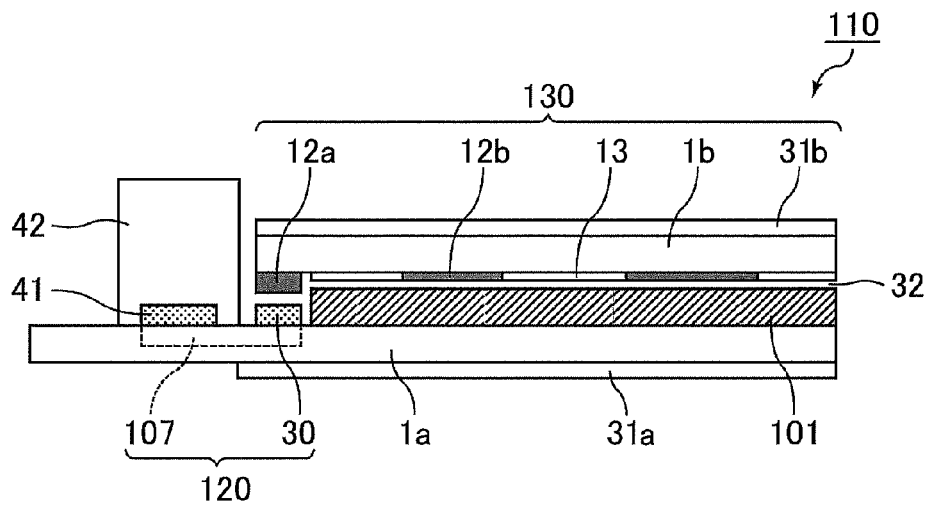
FIG. 2 is a schematic cross-sectional view illustrating a cross section of the ion sensor and the display device according to Embodiments 1 to 4.

The structure of the display device 110 is described using FIG. 2. FIG. 2 is a schematic cross-sectional view of the ion sensor and the display device which were cut along the line A1-A2 illustrated in FIG. 1. The ion sensor 120 is provided with the ion sensor circuit 107, an air ion lead-in/lead-out path 42, a fan (not illustrated), and a light-shielding film 12a (first light-shielding film). The ion sensor circuit 107 contains the ion sensor element that includes a sensor TFT (first FET) 30 and an ion sensor antenna 41. The display 130 is provided with the TFT array 101 including pixel TFTs (second FETs) 40, a light-shielding film 12b (second light-shielding film), a color filter 13 including colors such as RGB and RGBY, liquid crystals 32, and polarizers 31a and 31b.

The antenna 41 is a conductive member for detecting (capturing) negative ions in the air, and is connected to the gate of the sensor TFT 30. The antenna 41 includes a portion to be exposed to the external environment (exposure portion). Negative ions adhering to the surface (exposure portion) of the antenna 41 change the electric potential of the antenna 41, which changes the electric potential of the gate of the sensor TFT 30. As a result, the electric current and/or voltage between the source and drain in the sensor TFT 30 change(s). Thus, an ion sensor element including the antenna 41 and the sensor TFT 30 can be miniaturized compared to the conventional parallel plate ion sensor.

The lead-in/lead-out path 42 is a path for efficiently ventilating the space above the antenna 41. The fan blows air from the observation side to the depth side of FIG. 2, or from the depth side to the observation side.

The display device 110 is provided with two insulating substrates 1a and 1b which face each other in the most part, and the liquid crystals 32 disposed between the substrates 1a and 1b. The sensor TFT 30 and the TFT array 101 are provided on the main surface on the liquid crystal side of the substrate 1a (TFT array substrate) in the region where the substrates 1a and 1b face each other. The TFT array 101 includes pixel TFTs 40 arranged in a matrix state. The antenna 41, lead-in/lead-out path 42, and fan are arranged on the liquid crystal-side main surface of the substrate 1a in the region where the substrates 1a and 1b do not face each other. In this way, the antenna 41 is formed outside the channel regions of the sensor TFT 30. Thereby, the antenna 41 can be easily arranged near the lead-in/lead-out path 42 and the fan, efficiently sending air to the antenna 41. Also, the sensor TFT 30 and the light-shielding film 12a are formed at the end (picture-frame region) of the display 130. The arrangement leads to effective use of the space in the picture-frame region, and therefore the ion sensor circuit 107 can be formed without a change of the size of the display device 110.

On the one same main surface of the substrate 1a, at least the sensor TFT 30 and the ion sensor antenna 41 included in the ion sensor circuit 107, and the TFT array 101 included in the display-driving circuit 115 are formed. Accordingly, the sensor TFT 30 and the ion sensor antenna 41 can be formed using the process of forming the TFT array 101.

The light-shielding films 12a and 12b and the color filter 13 are provided on the liquid crystal-side main surface of the substrate 1b (counter substrate) in the region where the substrates 1a and 1b face each other. The light-shielding film 12a is formed at a position facing the sensor TFT 30, and the light-shielding film 12b and the color filter 13 are formed at a position facing the TFT array 101. The sensor TFT 30 includes a-Si which is a semiconductor whose properties are changed by light, as described in more detail later. Shielding the sensor TFT 30 from light with the light-shielding film 12a enables to reduce the property change of a-Si, i.e., the output property change of the sensor TFT 30. Thereby, the ion concentration can be measured with higher precision.

The polarizers 31a and 31b are formed on the respective main surfaces on the opposite side to the liquid crystals (outer side) of the substrates 1a and 1b.

Figure 3:
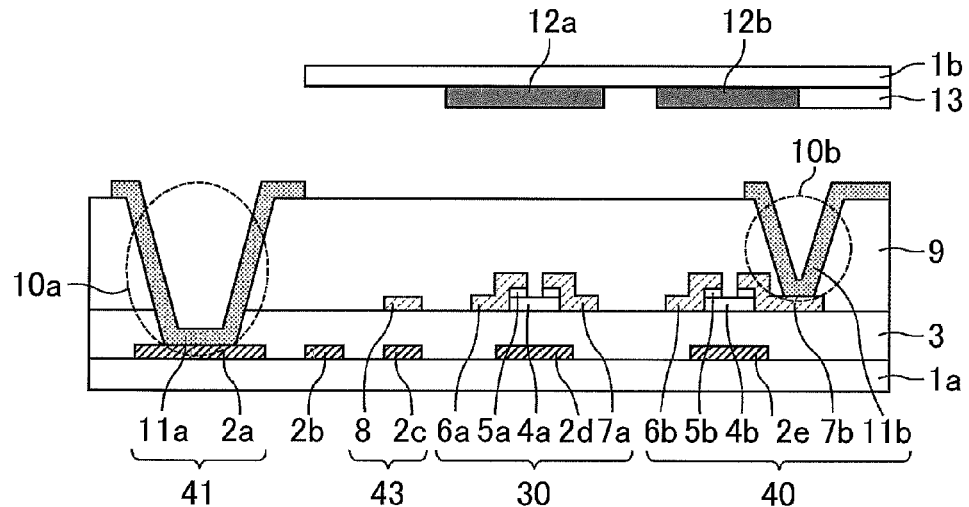
FIG. 3 is a schematic cross-sectional view illustrating a cross section of an ion sensor and a display device according to Embodiments 1 and 2.

The structure of the display device 110 is described in more detail with reference to FIG. 3. FIG. 3 is a schematic cross-sectional view of the ion sensor and the display device according to the present embodiment.

On the liquid crystal-side main surface of the insulating substrate 1a, a first conductive layer, an insulating film 3, a hydrogenated a-Si layer, an n+a-Si layer, a second conductive layer, a passivation film 9, and a third conductive layer are stacked in the stated order.

In the first conductive layer, an ion sensor antenna electrode 2a, a reset line 2b, a later-described connection line 22, a node-Z storage capacitor electrode 2c, and gate electrodes 2d and 2e are formed. These electrodes are formed in the first conductive layer, and can be formed by, for example, sputtering and photolithography from the same material through the same process. The first conductive layer is formed from a single or multiple metal layers. Specific examples of the first conductive layer include a single aluminum (Al) layer, a laminate of lower layer of Al/upper layer of titanium (Ti), and a laminate of lower layer of Al/upper layer of molybdenum (MO). The reset line 2b, the connection line 22, and the storage capacitor electrode 2c are described below in more detail with reference to FIG. 4.

The insulating film 3 is formed on the substrate 1a in such a manner as to cover the ion sensor antenna electrode 2a, the reset line 2b, the connection line 22, the node-Z storage capacitor electrode 2c, and the gate electrodes 2d and 2e. On the insulating film 3, hydrogenated a-Si layers 4a and 4b, n+a-Si layers 5a and 5b, source electrodes 6a and 6b, drain electrodes 7a and 7b, and a node-Z storage capacitor electrode 8 are formed. The source electrodes 6a and 6b, the drain electrodes 7a and 7b, and the storage capacitor electrode 8 are formed in the second conductive layer, and can be formed by sputtering and photolithography from the same material through the same process. The second conductive layer is formed from a single or multiple metal layers. Specific examples of the second conductive layer include a single aluminum (Al) layer, a laminate of lower layer of Al/upper layer of Ti, and a laminate of lower layer of Ti/upper layer of Al. The hydrogenated a-Si layers 4a and 4b can be formed by, for example, chemical vapor deposition (CVD) and photolithography from the same material through the same process. The n+a-Si layers 5a and 5b can also be formed by, for example, CVD and photolithography from the same material through the same process. In this way, at least part of the materials and processes can be the same in forming the electrodes and semiconductors. The cost required in formation of the sensor TFT 30 and the pixel TFTs 40 including the electrodes and semiconductors therefore can be reduced. The components of the TFTs 30 and 40 are described in more detail later.

The passivation film 9 is formed on the insulating film 3 in such a manner as to cover the hydrogenated a-Si layers 4a and 4b, n+a-Si layers 5a and 5b, source electrodes 6a and 6b, drain electrodes 7a and 7b, and storage capacitor electrode 8. On the passivation film 9, a transparent conductive film 11a (first transparent conductive film) and a transparent conductive film lib (second transparent conductive film) are formed. The transparent conductive film 11a is connected to the antenna electrode 2a via a contact hole 10a that penetrates the insulating film 3 and the passivation film 9. The transparent conductive film 11a is arranged to prevent the antenna electrode 2a from being exposed to the external environment because of the contact hole 10a. Hence, the arrangement makes it possible to prevent corrosion of the antenna electrode 2a as a result of being exposed to the external environment. The transparent conductive film 11b is connected to the drain electrode 7b via a contact hole 10b which penetrates the passivation film 9. These transparent electrodes 11a and 11b are formed in the third conductive layer, and can be formed by, for example, sputtering and photolithography from the same material through the same process. The third conductive layer is formed from a single or multiple transparent conducing films. Specific examples of the transparent conductive films include ITO films and IZO films. The materials constituting the transparent conductive films 11a and 11b are not required to be completely the same as each other. The processes for forming the transparent conductive films 11a and 11b are not required to be completely the same as each other either. For example, in the case that the transparent conductive film 11a and/or the transparent conductive film 11b have/has a multilayer structure, it is also possible to form only layer(s) common to the two transparent conductive films from the same material through the same process. Applying at least part of the materials and processes for forming the transparent conductive film 11b as described above to formation of the transparent conductive film 11a enables to form the transparent conductive film 11a at a low cost.

The light-shielding film 12a and the light-shielding film 12b can also be formed from the same material through the same process. Specifically, the light-shielding films 12a and 12b are formed from opaque metal (e.g. chromium (Cr)) films, opaque resin films, or other films. Examples of the resin films include acrylic resins containing carbon. Applying at least part of the materials and processes for forming the light-shielding film 12b as described above to formation of the light-shielding film 12a enables to form the light-shielding film 12a at a low cost.

The components of the TFTs 30 and 40 are described in more detail. The sensor TFT 30 is formed from the gate electrode 2d, the insulating film 3, the hydrogenated a-Si layer 4a, the n+a-Si layer 5a, the source electrode 6a, and the drain electrode 7a. The pixel TFTs 40 each are formed from the gate electrode 2e, the insulating film 3, the hydrogenated a-Si layer 4b, the n+a-Si layer 5b, the source electrode 6b, and the drain electrode 7b. The insulating film 3 functions as a gate insulating film in the sensor TFT 30 and the pixel TFTs 40. The TFTs 30 and 40 are bottom-gate TFTs. The n+a-Si layers 5a and 5b are doped with a V group element such as phosphorus (P). That is, the sensor TFT 30 and the pixel TFTs 40 are N-channel TFTs.

The antenna 41 is formed from the transparent conductive film 11a and the antenna electrode 2a. Further, a node-Z storage capacitor 43 (capacitor) is formed from the node-Z storage capacitor electrodes 2c and 8 and the insulating film 3 that functions as a dielectric. The capacitor electrode 2c is connected to the gate electrode 2d and the antenna electrode 2a, and the capacitor electrode 8 is grounded. Since it is possible to increase the capacitance of the gate electrode 2d and the antenna 41 by providing the capacitor 43, the influence of external noise during measurement of an ion concentration can be suppressed. Accordingly, the sensor operations can be made more stable and the accuracy can be further increased.

Figure 4:
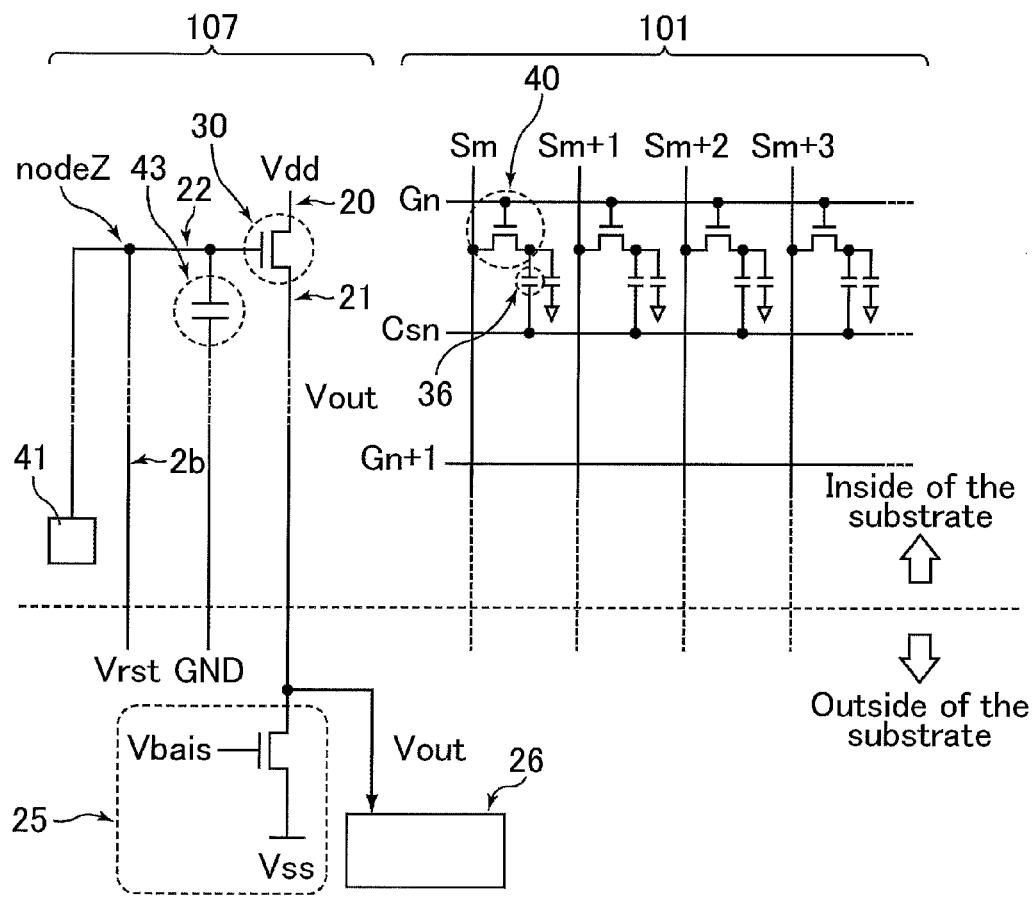
FIG. 4 is an equivalent circuit illustrating an ion sensor circuit 107 and a portion of a TFT array 101 according to Embodiments 1 and 2.

Next, the circuit configuration and the movement mechanism of the ion sensor circuit 107 and the TFT array 101 are described using FIG. 4. FIG. 4 is a view illustrating an equivalent circuit of portions of the ion sensor circuit 107 and the TFT array 101 according to the present embodiment.

First, the TFT array 101 is described. The gate electrodes 2d of the pixel TFTs 40 are connected to the gate driver 103 via the gate bus lines Gn, Gn+1, and so forth. The source electrodes 6b are connected to the source driver 104 via the source bus lines Sm, Sm+1, and so forth. The drain electrodes 7b of the pixel TFTs 40 are connected to the transparent conductive films lib which function as pixel electrodes. The pixel TFTs 40 are provided in the respective sub-pixels, and function as switching elements. The gate bus lines Gn, Gn+1, and so forth receive scanning pulses (scanning signals) in predetermined timings from the gate driver 103. The scanning pulses are applied to each pixel TFT 40 by a line sequential method. The source bus lines Sm, Sm+1, and so forth receive any image signals provided by the source driver 104 and/or display data calculated based on the negative ion concentration. Then, the image signals and/or display data are/is transmitted, in predetermined timing, to the pixel electrodes (transparent conductive films 11b) connected to the pixel TFTs 40 that are turned on for a certain period by inputted scanning pulses. The image signals and/or display data at a predetermined level written to the liquid crystals are stored for a certain period between the pixel electrodes having received these signals and/or data and the counter electrode (not illustrated) facing the pixel electrodes. Here, together with the liquid crystal capacitors formed between the pixel electrodes and the counter electrode, liquid crystal storage capacitors (Cs) 36 are formed. The liquid crystal storage capacitor 36 is formed between the drain electrode 7a and the liquid crystal auxiliary capacitor line Csn, Csn+1, or the like in the respective sub-pixels. The capacitor lines Csn, Csn+1, and so forth are formed in the first conductive layer, and are disposed in parallel with the gate lines Gn, Gn+1, and so forth.

Next, the circuit configuration of the ion sensor circuit 107 will be described. An input line 20 is connected to the drain electrode 7a of the sensor TFT 30. A high voltage (+10 V) or a low voltage (0 V) is applied to the input line 20, and the voltage of the input line 20 is taken as Vdd. An output line 21 is connected to the source electrode 6a. The voltage of the output line 21 is taken as Vout. Further, the antenna 41 is connected through the connection line 22 to the gate electrode 2d of the sensor TFT 30. The reset line 2b is also connected to the connection line 22. A point of intersection (node) between the lines 22 and 2b is taken as a node-Z. The reset line 2b is a line for resetting the node-Z, that is, a voltage between the gate of the sensor TFT 30 and the antenna 41. A high voltage (+20 V) or a low voltage (−10 V) is applied to the reset line 2b, and the voltage of the reset line 2b is taken as Vrst. In addition, a ground (GND) is connected to the connection line 22 through the storage capacitor 43. A constant current circuit 25 and an analog-digital conversion circuit (ADC) 26 are connected to the output line 21. The constant current circuit 25 is constituted by an N-channel TFT (constant current TFT), and a drain of the constant current TFT is connected to the output line 21. A source of the constant current TFT is connected to a constant current source, and a voltage Vss thereof is fixed to a voltage that is lower than the high voltage of Vdd. A gate of the constant current TFT is connected to a constant voltage source. A voltage Vbais of the gate of the constant current TFT is fixed to a predetermined value so that a constant current (for example, 1 µA) flows between the source and drain of the constant current TFT. The constant current circuit 25 and the ADC 26 are formed inside the driving/reading circuit 105.

The antenna electrode 2a, the gate electrode 2d, the reset line 2b, the storage capacitor electrode 2c, and the connection line 22 are integrally formed in the first conductive layer such that the antenna 41, the gate of the sensor TFT 30, the reset line 2b, the connection line 22, and the storage capacitor 43 are connected to each other. In contrast, the driving/reading circuit 105, the gate driver 103, and the source driver 104 each are not formed directly on the substrate 1a, but are formed on a semiconductor chip. The semiconductor chip is then mounted on the substrate 1a.

Figure 5:
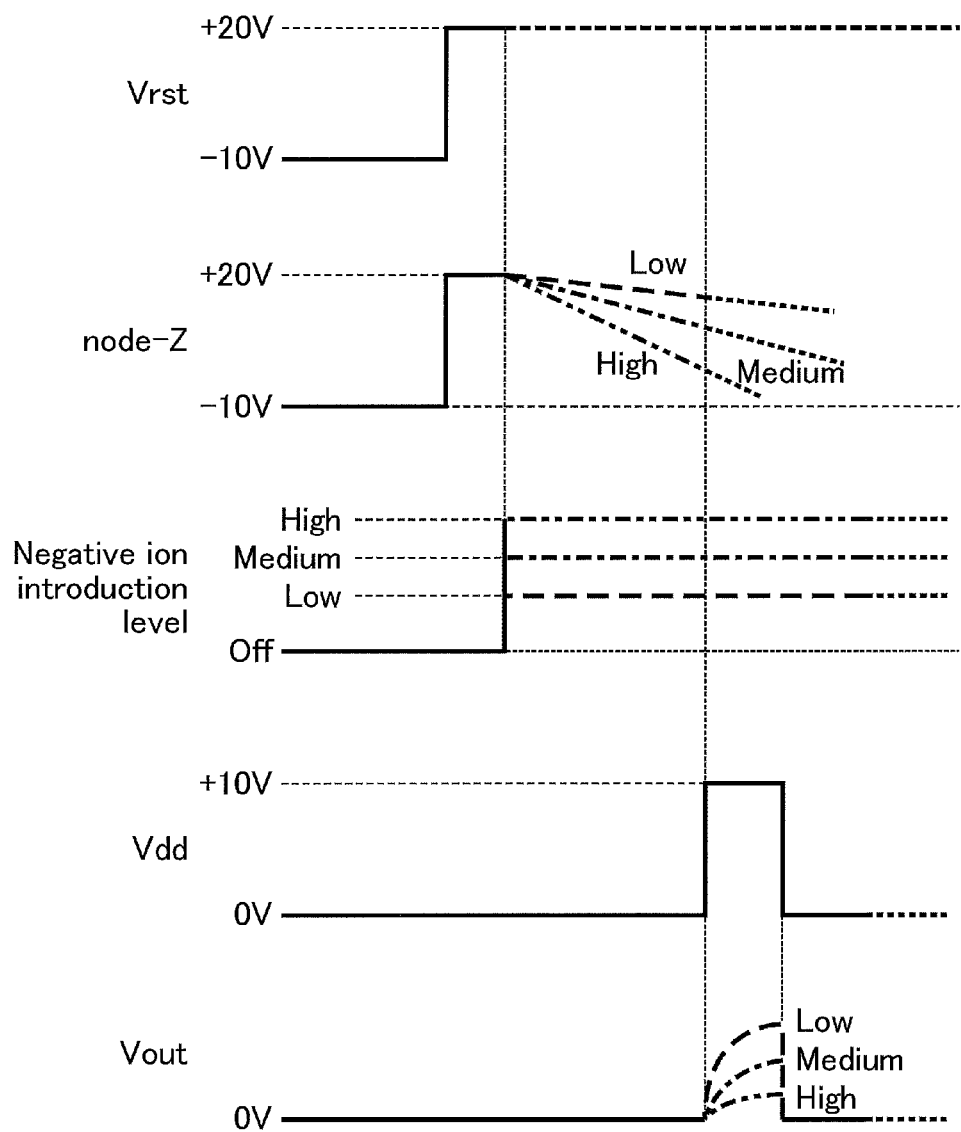
FIG. 5 is a timing chart of the ion sensor circuit according to Embodiment 1.

Next, the operational mechanism of the ion sensor circuit is described in detail using FIG. 5. FIG. 5 is a timing chart of the ion sensor circuit according to the present embodiment.

In the initial state, Vrst is set to a low voltage (−10 V). At this time, a power supply for applying a low voltage (−10 V) to the gate electrode 2e of the pixel TFT 40 can also be used as a power supply for setting Vrst to the low voltage (−10 V). Further, in the initial state Vdd is set to a low voltage (0 V). Before starting measurement of an ion concentration, first, a high voltage (+20 V) is applied to the reset line 2b by the reset device and the voltage of the antenna 41 (voltage of the node-Z) is reset to +20 V. At this time, a power supply for applying a high voltage (+20 V) to the gate electrode 2e of the pixel TFT 40 can also be used as a power supply for applying Vrst. After the voltage of the node-Z has been reset, the reset line 2b is held in a high impedance state by the reset device. Subsequently, when introduction of ions starts and negative ions are captured by the antenna 41, the voltage of the node-Z that has been reset to +20 V, that is, charged to a positive voltage, is neutralized by the negative ions and decreases (sensing operation). The higher the negative ion concentration is, the faster the speed at which the voltage decreases. After a predetermined time period has elapsed since introduction of ions began, a high voltage (+10 V) is temporarily applied to the input line 20. That is, a pulse voltage of +10 V is applied to the input line 20. In addition, the output line 21 is connected to the constant current circuit 25. Accordingly, when a pulse voltage of +10 V is applied to the input line 20, a constant current flows in the input line 20 and the output line 21. However, a voltage Vout of the output line 21 varies in accordance with the degree of opening of the gate of the sensor TFT 30, that is, a difference in the voltage of the node-Z. By detecting the voltage Vout with the ADC 26, it is possible to detect the negative ion concentration. In this connection, it is also possible to adopt a configuration in which the constant current circuit 25 is not provided, and a negative ion concentration is detected by detecting a current Id of the output line 21 that varies in accordance with a difference in the voltage of the node-Z.

The configuration and operational mechanism of the reset device will now be described.

Figure 6:
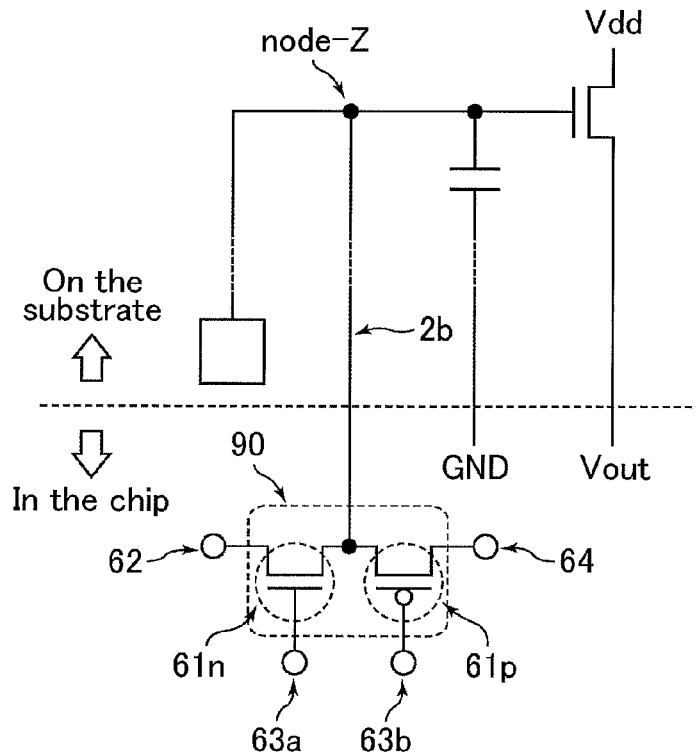
FIG. 6 is an equivalent circuit illustrating a reset device according to Embodiments 1, 3 and 4.

As shown in FIG. 6, a reset device 90 is constituted by an N-channel MOSFET 61n and a P-channel MOSFET 61p as switching elements that are formed inside the drive/read circuit 105, that is, in the semiconductor chip. A source of the MOSFET 61n is connected to the reset line 2b, a drain of the MOSFET 61n is connected to a power supply 62 of +20 V, and a gate of the MOSFET 61n is connected to a control signal source 63a. A source of the MOSFET 61p is connected to the reset line 2b, a drain of the MOSFET 61p is connected to a power supply 64 of −10 V, and a gate of the MOSFET 61p is connected to a control signal source 63b.

Figure 7:
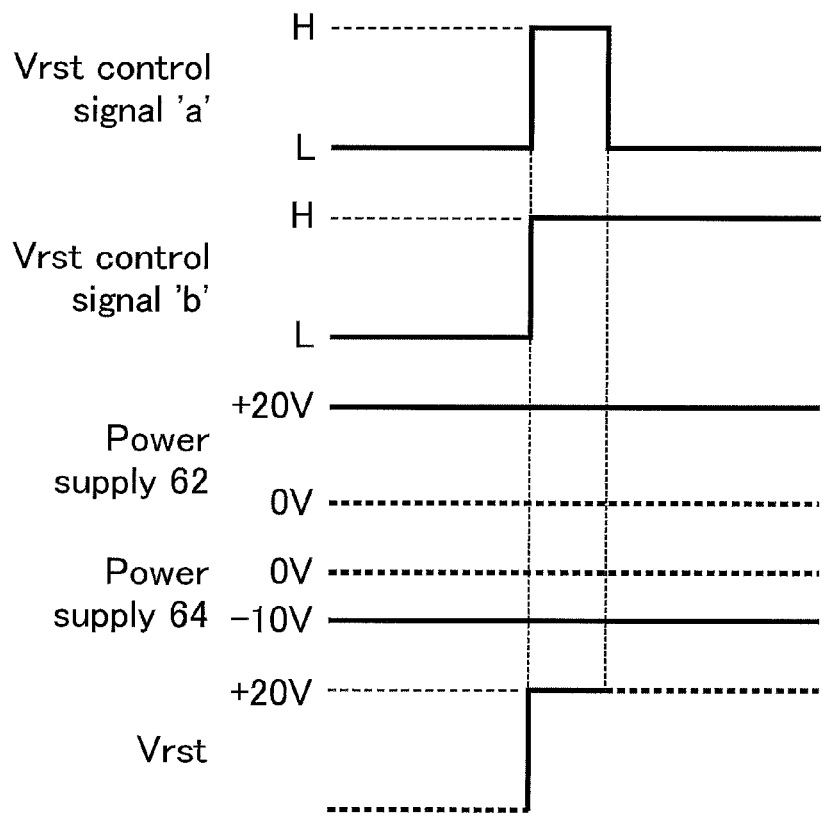
FIG. 7 is a timing chart of the reset device according to Embodiments 1, 3 and 4.

As shown in FIG. 7, the control signal source 63b inputs a Vrst control signal 'b' to the MOSFET 61p. In the initial state, the Vrst control signal 'b' is set to a low voltage and the MOSFET 61p is in an 'on' state. Accordingly, in the initial state, Vrst is set to −10 V. Immediately before measurement of an ion concentration is started, the control signal source 63a inputs a Vrst control signal 'a' that is a pulse signal to the MOSFET 61n. In synchrony with the input of the Vrst control signal 'a', the Vrst control signal 'b' changes to a high voltage. As a result, the MOSFET 61p enters an 'off' state. On the other hand, the MOSFET 61n temporarily enters an 'on' state, and a high voltage of +20 V is applied to the reset line 2b. Since the MOSFET 61n enters an 'off' state after input of the Vrst control signal 'a', the reset line 2b, that is, the node-Z, maintains the high impedance state.

Modification examples of the reset device are described hereinafter.

Figure 8:
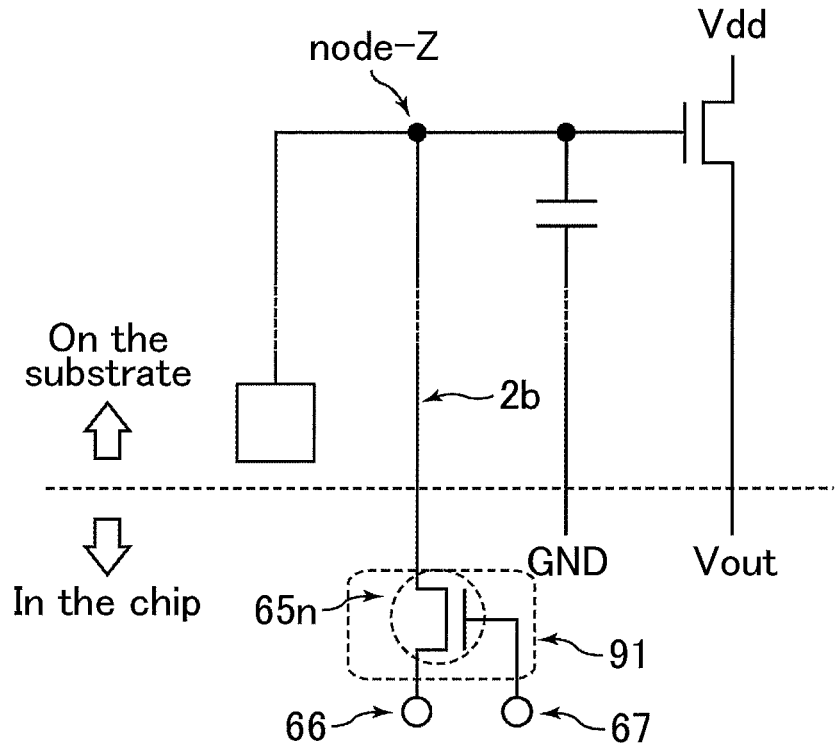
FIG. 8 is an equivalent circuit illustrating the reset device according to Embodiments 1, 3 and 4.

As shown in FIG. 8, a reset device 91 may be constituted by an N-channel MOSFET 65n as a switching element that is formed inside the drive/read circuit 105, that is, inside the semiconductor chip. A source of the MOSFET 65n is connected to the reset line 2b, a drain of the MOSFET 65n is connected to a power supply 66 of +20 V, and a gate of the MOSFET 65n is connected to a control signal source 67.

Figure 9:
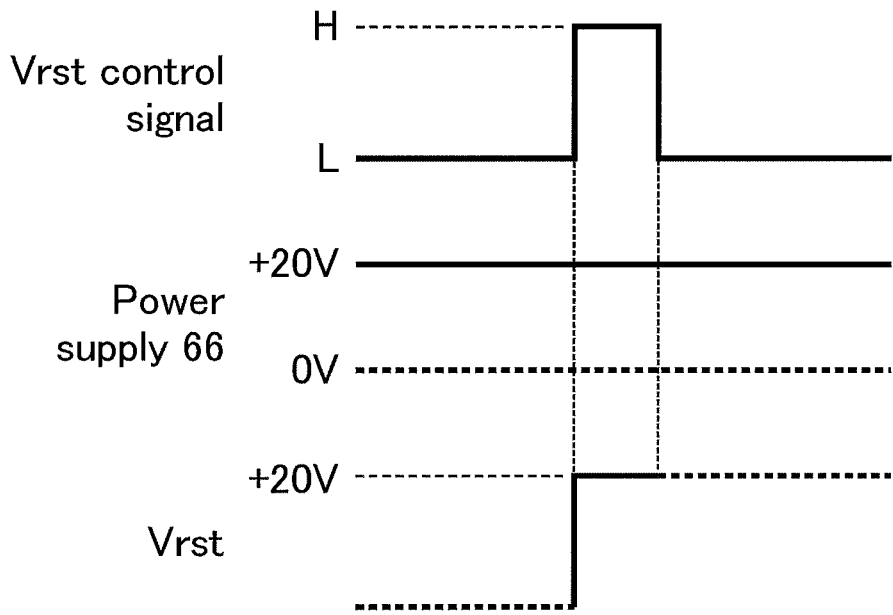
FIG. 9 is a timing chart of the reset device according to Embodiments 1, 3 and 4.

As shown in FIG. 9, the control signal source 67 inputs a Vrst control signal that is a pulse signal to the MOSFET 65n. As a result, the MOSFET 65n temporarily enters an 'on' state, and a high voltage of +20 V is applied to the reset line 2b. Since the MOSFET 65n enters an 'off' state after input of the Vrst control signal, the reset line 2b, that is, the node-Z, maintains the high impedance state.

Note that according to the present modification example, although there is no means that controls Vrst in the initial state, this does not constitute a particular problem as measurement of an ion concentration is not affected.

Further, if the resistances in the 'off' state of the MOSFETs 61n and 61p are taken as R_L1a and R_L1b, respectively, and the resistance in the 'off' state of the MOSFET 65n is taken as R_L2, generally the relation R_L2>R_L1a>R_L1b exists between the sizes of the respective resistances. Accordingly, from the viewpoint of suppressing unwanted variations in the potential (noise) of the node-Z during ion concentration detection, the configuration illustrated in FIG. 8 is preferable to the configuration illustrated in FIG. 6.

Figure 10:
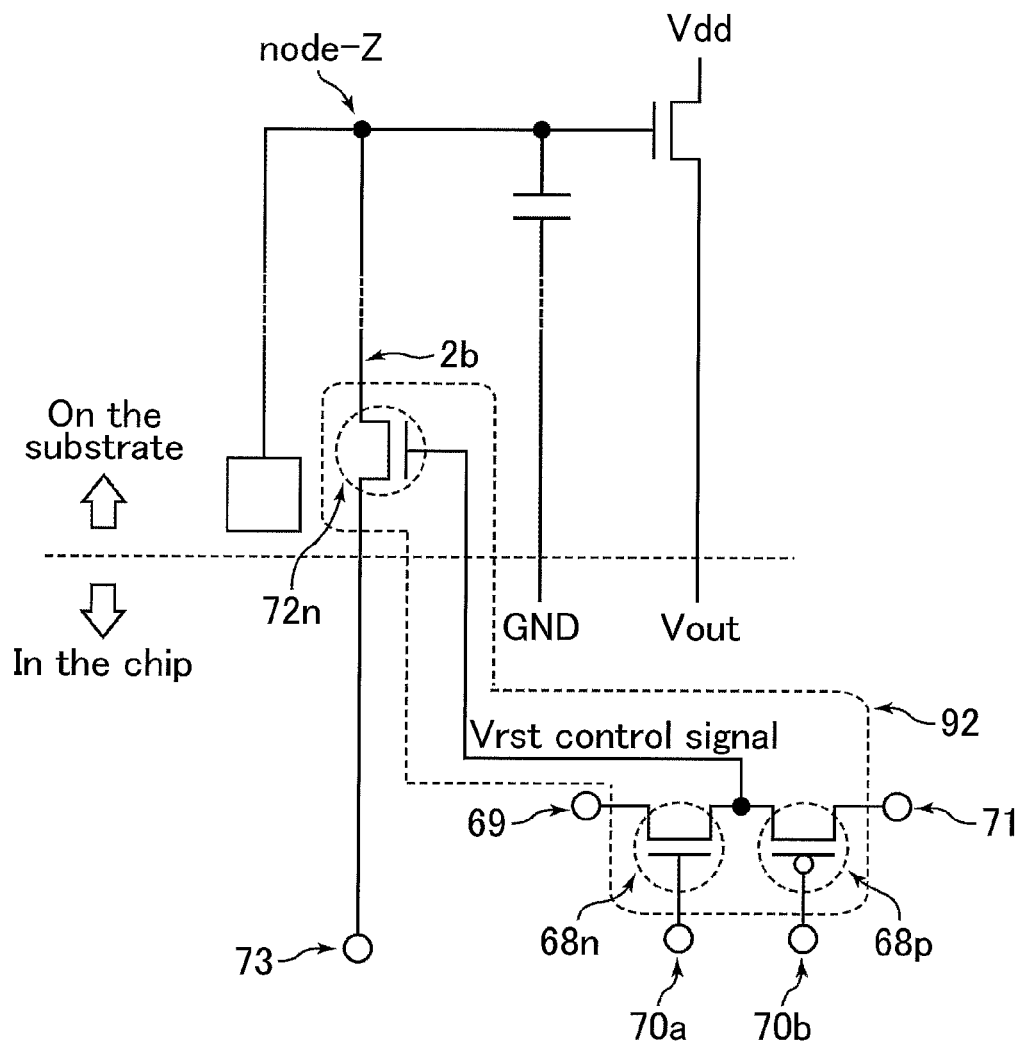
FIG. 10 is an equivalent circuit illustrating the reset device according to Embodiments 1, 3 and 4.

As shown in FIG. 10, a reset device 92 may be constituted from an N-channel MOSFET 68n, a P-channel MOSFET 68p, and an N-channel TFT 72n that are switching elements. The MOSFETs 68n and 68p are formed inside the driving/reading circuit 105, that is, inside the semiconductor chip, and the TFT 72n is formed on the substrate 1a. The source of the MOSFET 68n is connected to the gate of the TFT 72n, the drain of the MOSFET 68n is connected to a power supply 69 of +20 V, and the gate of the MOSFET 68n is connected to a control signal source 70a. The source of the MOSFET 68p is connected to the gate of the TFT 72n, the drain of the MOSFET 68p is connected to a power supply 71 of −10 V, and the gate of the MOSFET 68p is connected to a control signal source 70b. The source of the TFT 72n is connected to the reset line 2b, the drain of the TFT 72n is connected to a power supply 73 of +20 V, and the gate of the TFT 72n is connected to the respective sources of the MOSFETs 68n and 68p.

Figure 11:
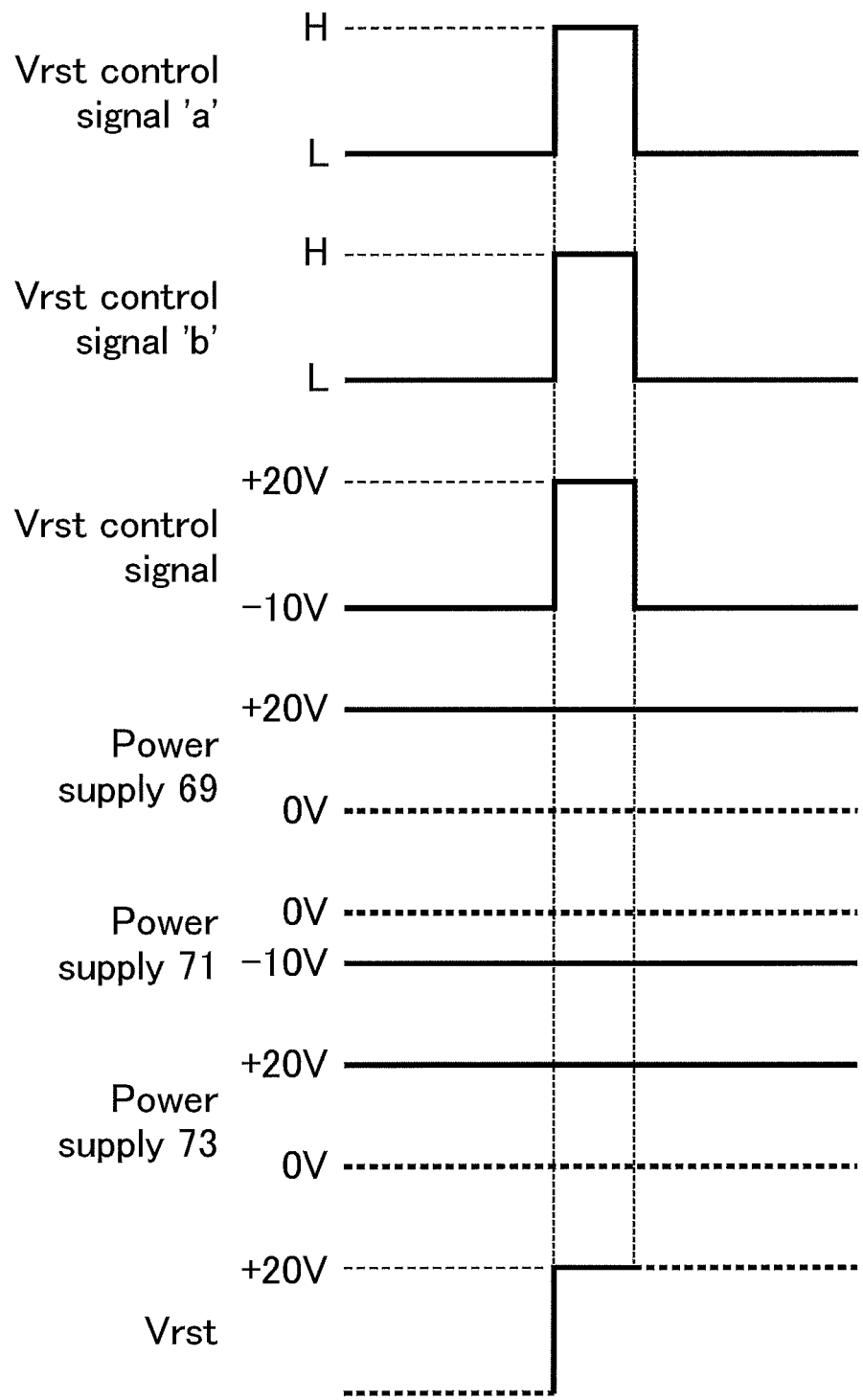
FIG. 11 is a timing chart of the reset device according to Embodiments 1, 3 and 4.

As shown in FIG. 11, the control signal source 70b inputs a Vrst control signal 'b' to the MOSFET 68p. In the initial state, the Vrst control signal 'b' is set to a low voltage and the MOSFET 68p is in an 'on' state. Accordingly, in the initial state, a Vrst composite signal that is applied to the gate of the TFT 72n is a low voltage of −10 V, and the TFT 72n is in an 'off' state. Immediately before measurement of an ion concentration is started, the control signal source 70a inputs a Vrst control signal 'a' that is a pulse signal to the MOSFET 68n. Further, in synchrony with the input of the Vrst control signal 'a', the Vrst control signal 'b' temporarily changes to a high voltage. As a result, the MOSFET 68p temporarily enters an 'off' state. On the other hand, the MOSFET 68n temporarily enters an 'on' state, and the Vrst composite signal becomes a high voltage of +20 V. As a result, the TFT 72n temporarily enters an 'on' state, and a high voltage of +20 V is applied to the reset line 2b. Subsequently, when each of the Vrst control signals 'a' and 'b' returns to a low voltage, the MOSFET 68p enters an 'on' state and the TFT 72n enters an 'off' state, and hence the reset line 2b, that is, the node-Z, maintains the high impedance state.

Figure 12:
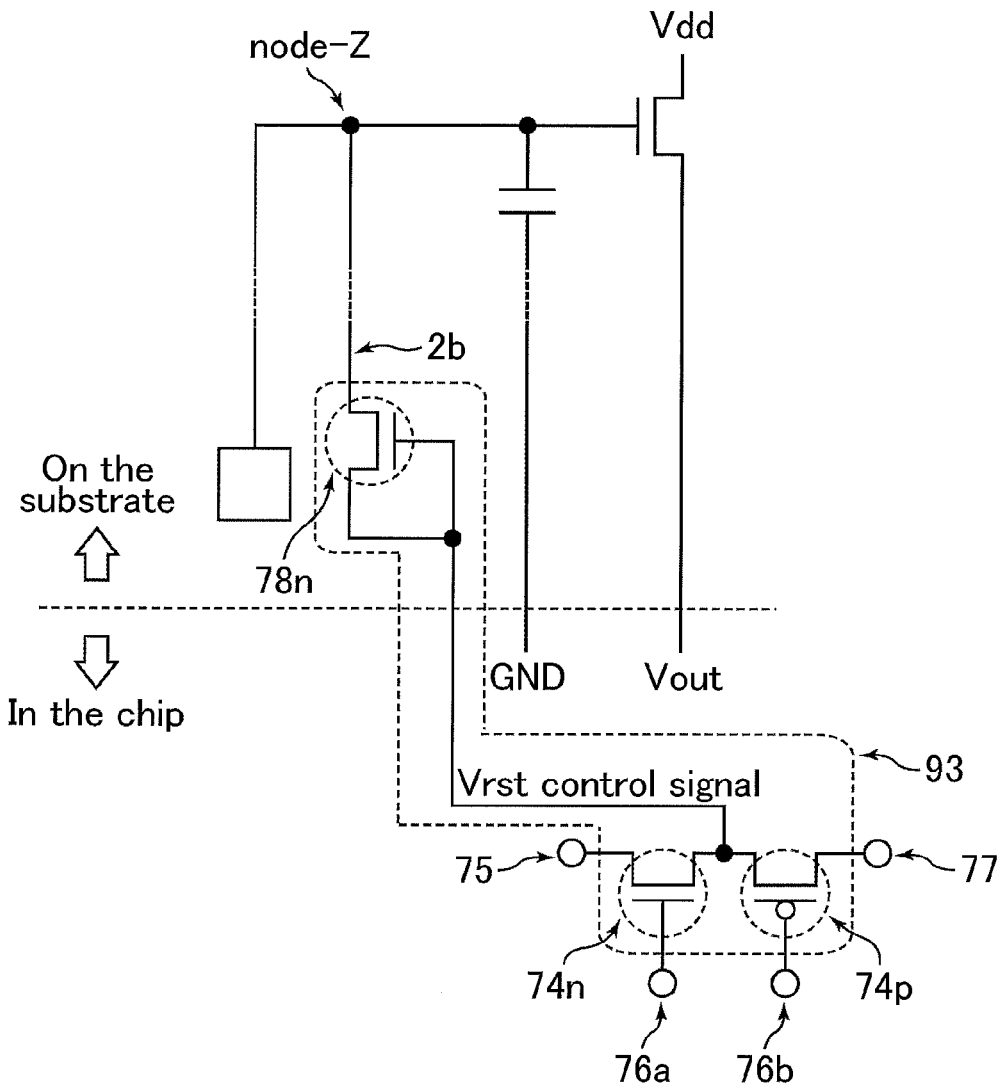
FIG. 12 is an equivalent circuit illustrating the reset device according to Embodiments 1, 3 and 4.

As shown in FIG. 12, a reset device 93 may be constituted from an N-channel MOSFET 74n, a P-channel MOSFET 74p, and an N-channel TFT 78n that are switching elements. The MOSFETs 74n and 74p are formed inside the driving/reading circuit 105, that is, inside the semiconductor chip, and the TFT 78n is formed on the substrate 1a. The source of the MOSFET 74n is connected to the gate of the TFT 78n, the drain of the MOSFET 74n is connected to a power supply 75 of +20 V, and the gate of the MOSFET 74n is connected to a control signal source 76a. The source of the MOSFET 74p is connected to the gate of the TFT 78n, the drain of the MOSFET 74p is connected to a power supply 77 of −10 V, and the gate of the MOSFET 74p is connected to a control signal source 76b. The source of the TFT 78n is connected to the reset line 2b, the drain of the TFT 78n is short-circuited with the gate, and the gate of the TFT 78n is connected to the respective sources of the MOSFETs 74n and 74p.

Figure 13:
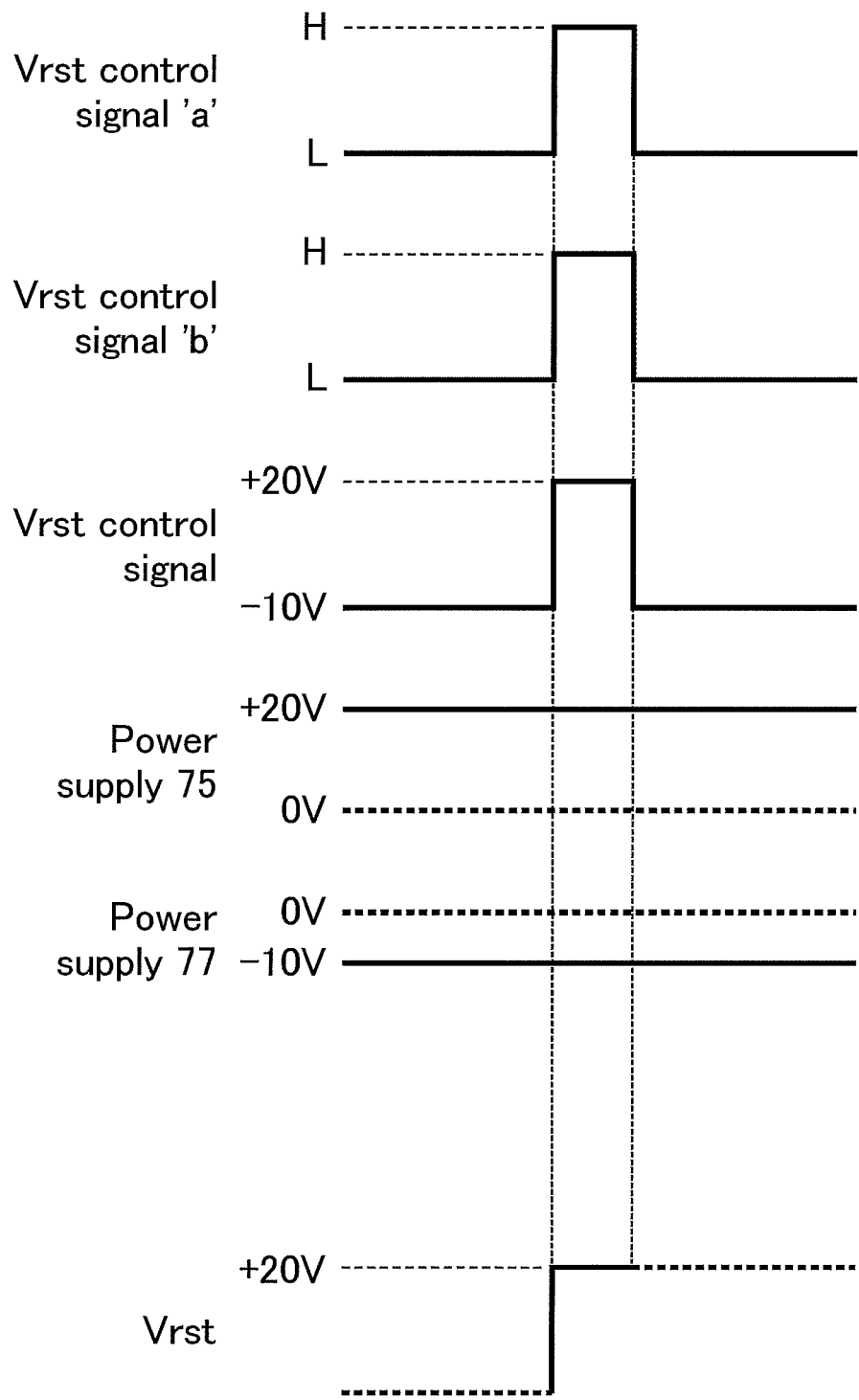
FIG. 13 is a timing chart of the reset device according to Embodiments 1, 3 and 4.

As shown in FIG. 13, the control signal source 76b inputs the Vrst control signal 'b' to the MOSFET 74p. In the initial state, the Vrst control signal 'b' is set to a low voltage and the MOSFET 74p is in an 'on' state. Accordingly, in the initial state, a Vrst composite signal that is applied to the gate of the TFT 78n is a low voltage of −10 V, and the TFT 78n is in an 'off' state. Immediately before measurement of an ion concentration is started, the control signal source 76a inputs a Vrst control signal 'a' that is a pulse signal to the MOSFET 74n. Further, in synchrony with the input of the Vrst control signal 'a', the Vrst control signal 'b' temporarily changes to a high voltage. As a result, the MOSFET 74p temporarily enters an 'off' state. On the other hand, the MOSFET 74n temporarily enters an 'on' state, and the Vrst composite signal becomes a high voltage of +20 V. As a result, the TFT 78n temporarily enters an 'on' state, and a high voltage of +20 V is applied to the reset line 2b. Subsequently, when each of the Vrst control signals 'a' and 'b' returns to a low voltage, the MOSFET 74p enters an 'on' state and the TFT 78n enters an 'off' state, and hence the reset line 2b, that is, the node-Z, maintains the high impedance state.

Figure 14:
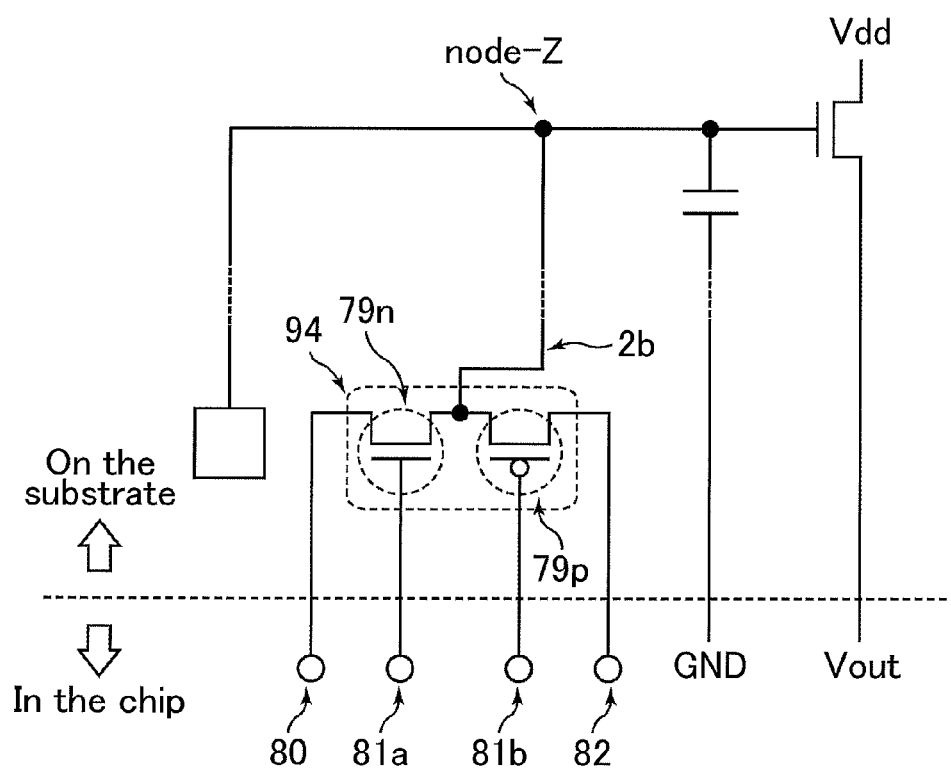
FIG. 14 is an equivalent circuit illustrating the reset device according to Embodiments 1, 3 and 4.

As shown in FIG. 14, a reset device 94 may be constituted from an N-channel TFT 79n and a P-channel TFT 79p that are switching elements and that are formed on the substrate 1a. The source of the TFT 79n is connected to the reset line 2b, the drain of the TFT 79n is connected to a power supply 80 of +20 V, and the gate of the TFT 79n is connected to a control signal source 81a. The source of the TFT 79p is connected to the reset line 2b, the drain of the TFT 79p is connected to a power supply 82 of −10 V, and the gate of the TFT 79p is connected to a control signal source 81b.

Figure 15:
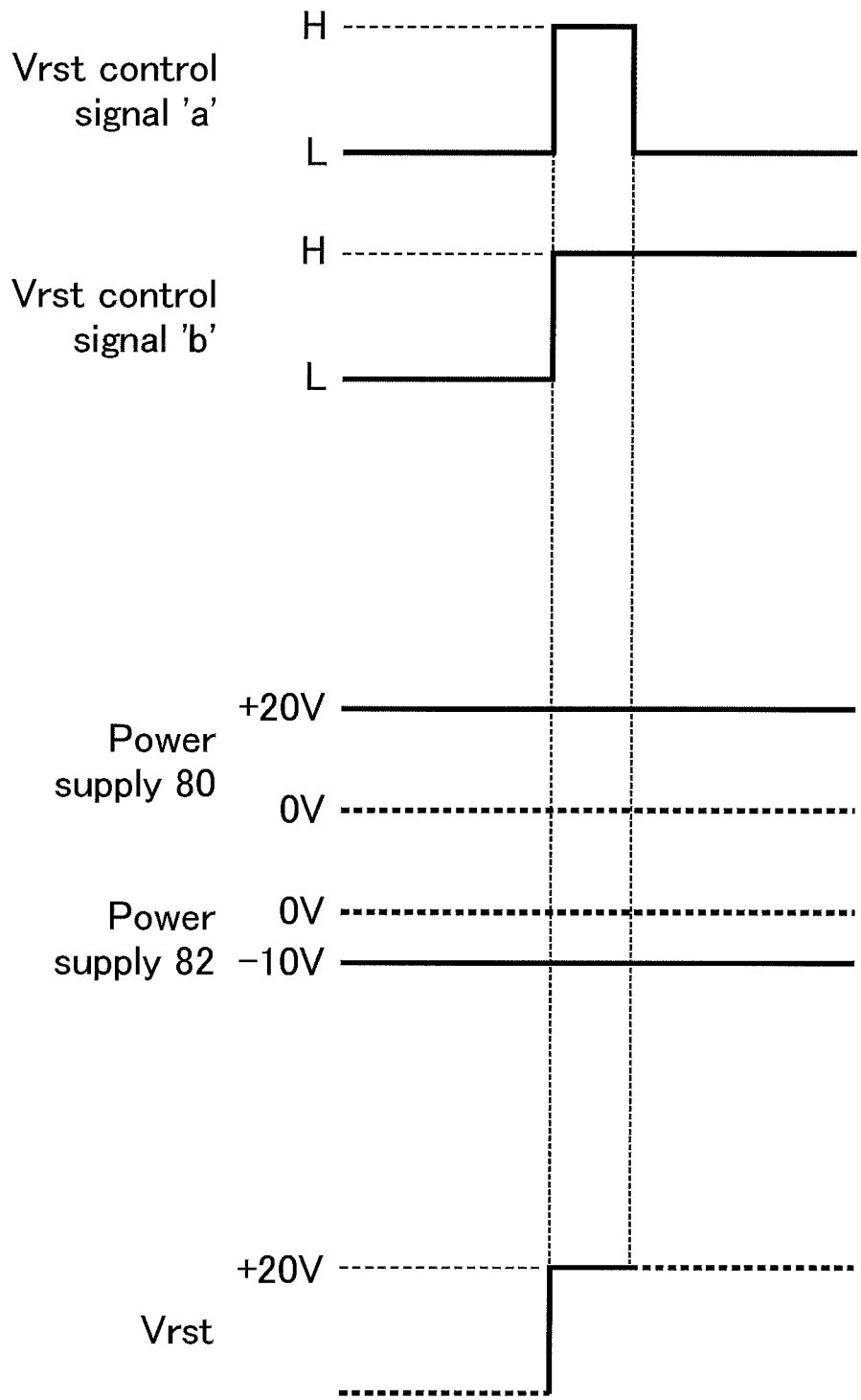
FIG. 15 is a timing chart of the reset device according to Embodiments 1, 3 and 4.

As shown in FIG. 15, the control signal source 81b inputs a Vrst control signal 'b' to the TFT 79p. In the initial state, the Vrst control signal 'b' is set to a low voltage and the TFT 79p is in an 'on' state. Accordingly, in the initial state, Vrst is set to −10 V. Immediately before measurement of an ion concentration is started, the control signal source 81a inputs a Vrst control signal 'a' that is a pulse signal to the TFT 79n. In synchrony with the input of the Vrst control signal 'a', the Vrst control signal 'b' changes to a high voltage. As a result, the TFT 79p enters an 'off' state. On the other hand, the TFT 79n temporarily enters an 'on' state, and a high voltage of +20 V is applied to the reset line 2b. Since the TFT 79n enters an 'off' state after input of the Vrst control signal 'a', the reset line 2b, that is, the node-Z, maintains the high impedance state.

Note that according to the present modification examples, since it is necessary to form the N-channel and P-channel type TFTs on the substrate 1a, it is preferable to form a semiconductor layer that has high mobility, such as a p-Si layer, as the semiconductor layer.

In addition, according to the present modification examples, it is necessary to from a CMOS circuit (not shown) in the driving/reading circuit 105, that is, in the semiconductor chip, in order to generate the Vrst control signals 'a' and 'b'.

Further, if the resistance in an 'off' state of the TFT 72n is taken as R_P1, the resistance in an 'off' state of the TFT 78n is taken as R_P2, and the resistances in the 'off' state of the TFTs 79n and 79p are taken as R_P3a and R_P3b, respectively, generally the relation R_P1≈R_P3a>R_P3b>R_P2 exists between the sizes of the respective resistances. Accordingly, from the viewpoint of suppressing unwanted variations in the potential of the node-Z (noise) during ion concentration detection, the configurations illustrated in FIGS. 10 and 14 are preferable to the configuration illustrated in FIG. 12.

In addition, in general, the resistance of a MOSFET formed inside a semiconductor chip is greater than the resistance of a TET that is formed on a substrate. Accordingly, from the viewpoint of improving a characteristic with respect to maintaining the potential of the node-Z, that is, maintaining the node-Z in a high impedance state more effectively, preferably a switching element that is directly connected to the reset line 2b (node-Z) is formed inside a semiconductor chip. As a result, unwanted variations in the potential of the node-Z (noise) during ion concentration detection can be suppressed to a greater degree.

Note that from the viewpoint of circuit simplification and cost reduction, there is no significant difference between the configurations in which all of the reset device is formed inside the semiconductor chip (FIGS. 6 and 8) and the configurations in which a portion of the reset device is formed on the substrate 1a (FIGS. 10, 12, and 14).

On the other hand, from the viewpoint of reducing variations with time in the properties and enhancing the reliability of the reset device, it is preferable to form a switching element that is directly connected to the reset line 2b (node-Z) inside the semiconductor chip.

Note that, according to the present embodiment, a high voltage of Vdd is not particularly limited to +10 V, and the high voltage of Vdd may be the same as a high voltage applied to the reset line 2b, that is, the same as the high voltage of +20 V that is applied to the gate electrode 2e of the pixel TFT 40. Thus, a power supply for applying the high voltage to the gate electrode 2e of the pixel TFT 40 can also be used as a power supply for applying the high voltage of Vdd.

(Embodiment 2)

A display device according to Embodiment 2 has the same configuration as Embodiment 1 except for the following points. That is, although the display device according to Embodiment 1 includes an ion sensor that is capable of measuring a negative ion concentration in the atmosphere using the N-channel sensor TFT 30, the display device according to Embodiment 2 includes an ion sensor that is capable of measuring a positive ion concentration in the atmosphere using a P-channel sensor TFT 30.

More specifically, p+a-Si layers are formed instead of the n+a-Si layers 5a and 5b, and the p+a-Si layers are doped with a third group element such as boron (B). That is, according to the present embodiment, the sensor TFT 30 and the pixel TFT 40 are P-channel TFTs.

Figure 16:
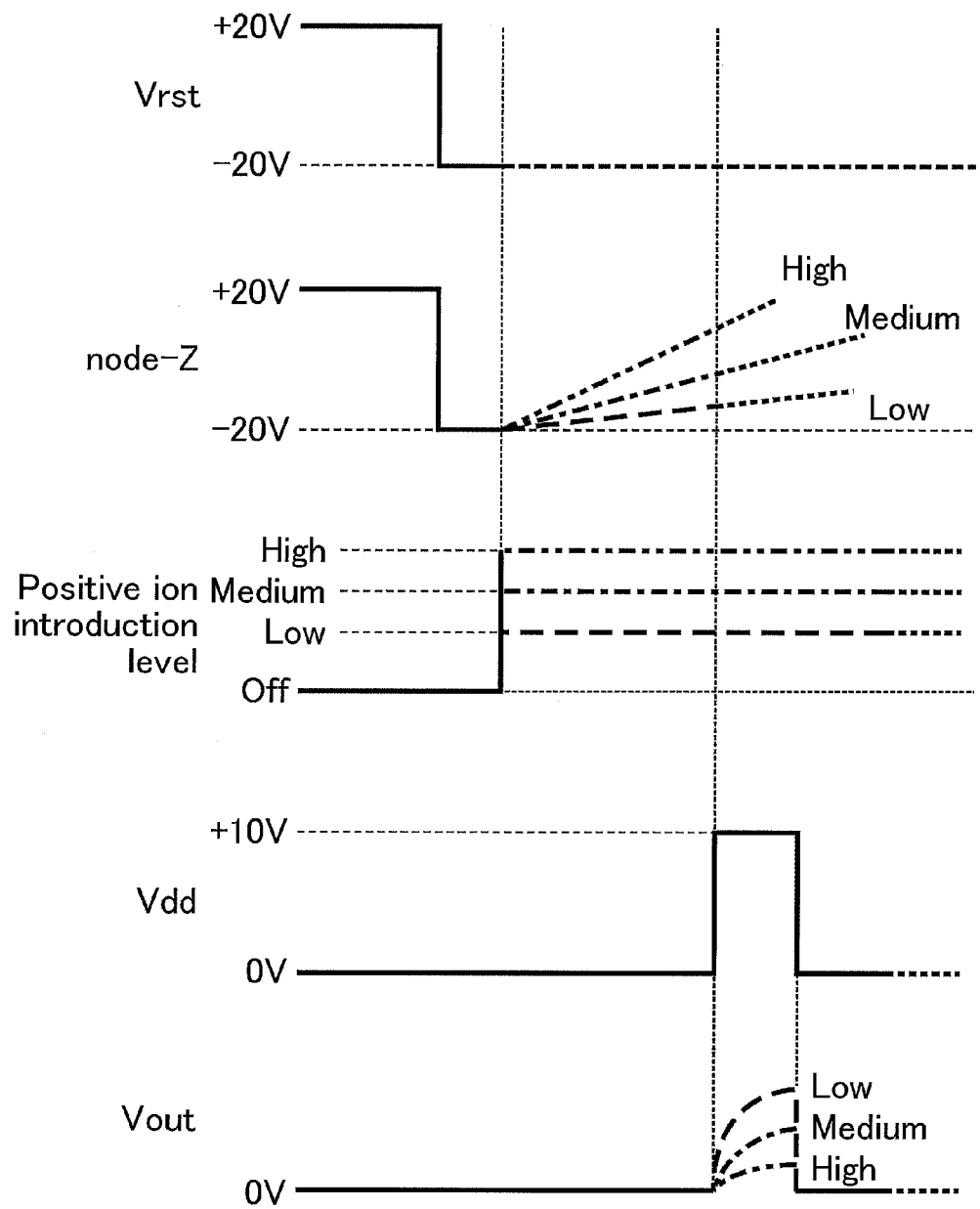
FIG. 16 is a timing chart of an ion sensor circuit according to Embodiment 2.

The operational mechanism of the ion sensor circuit will now be described in detail using FIG. 16. FIG. 16 is a timing chart of the ion sensor circuit according to the present embodiment.

In the initial state, Vrst is set to a high voltage (+20 V). At this time, a power supply for applying a high voltage (+20 V) to the gate electrode 2e of the pixel TFT 40 can also be used as a power supply for setting Vrst to the high voltage (+20V). Further, in the initial state, Vdd is set to a low voltage (0 V). Before starting measurement of an ion concentration, first a low voltage (−20 V) is applied to the reset line 2b by means of the reset device to reset the voltage of the antenna 41 (voltage of the node-Z) to −20 V. After the voltage of the node-Z has been reset, the reset line 2b is held in a high impedance state by means of the reset device. Subsequently, when an operation to introduce ions is commenced and positive ions are captured by the antenna 41, the voltage of the node-Z that has been reset to −20 V, that is, charged to a negative voltage, is neutralized by the positive ions and increases. The higher the positive ion concentration is, the faster the speed at which the voltage increases. After a predetermined time period has elapsed since introduction of ions began, a high voltage (+10 V) is temporarily applied to the input line 20. That is, a pulse voltage of +10 V is applied to the input line 20. Further, the output line 21 is connected to the constant current circuit 25. Accordingly, when a pulse voltage of +10 V is applied to the input line 20, a constant current flows in the input line 20 and the output line 21. However, the voltage Vout of the output line 21 varies in accordance with the degree of opening of the gate of the sensor TFT 30, that is, a difference in the voltage of the node-Z. By detecting the voltage Vout with the ADC 26, it is possible to detect the positive ion concentration. In this connection, it is also possible to adopt a configuration in which the constant current circuit 25 is not provided, and in which the positive ion concentration can be detected by detecting a current Id of the output line 21 that varies in accordance with a difference in the voltage of the node-Z.

In addition, the reset device of the present embodiment includes a MOSFET or a TFT of an opposite conductivity type to that of Embodiment 1, and is controlled by signals of opposite polarity to Embodiment 1.

Further, according to the present embodiment, the low voltage that is applied to the reset line 2b is not particularly limited to −20 V, and the low voltage may be −10 V that is the same as the low voltage applied to the gate electrode 2e of the pixel TFT 40. Thus, a power supply for applying a low voltage to the gate electrode 2e of the pixel TFT 40 can used be also as a power supply for applying a low voltage to be applied to the reset line 2b. In addition, the high voltage of Vdd is not particularly limited to +10 V, and the high voltage may be the same as the high voltage applied to the reset line 2b, that is, the same as the high voltage of +20 V that is applied to the gate electrode 2e of the pixel TFT 40. Thus, a power supply for applying a high voltage to the gate electrode 2e of the pixel TFT 40 can also be used as a power supply for applying the high voltage of Vdd.

(Embodiment 3)

A display device according to Embodiment 3 has the same configuration as Embodiment 1, except for the following points. That is, the display device according to Embodiment 1 includes an ion sensor (hereinafter, also referred to as "single-gate sensor") of a type that uses a TFT in which a gate electrode is formed only on one side of a semiconductor layer. In contrast, the display device according to Embodiment 3 includes an ion sensor (hereinafter, also referred to as "double-gate sensor") of a type that uses a TFT in which gate electrodes are formed on both sides of a semiconductor layer.

Figure 17:
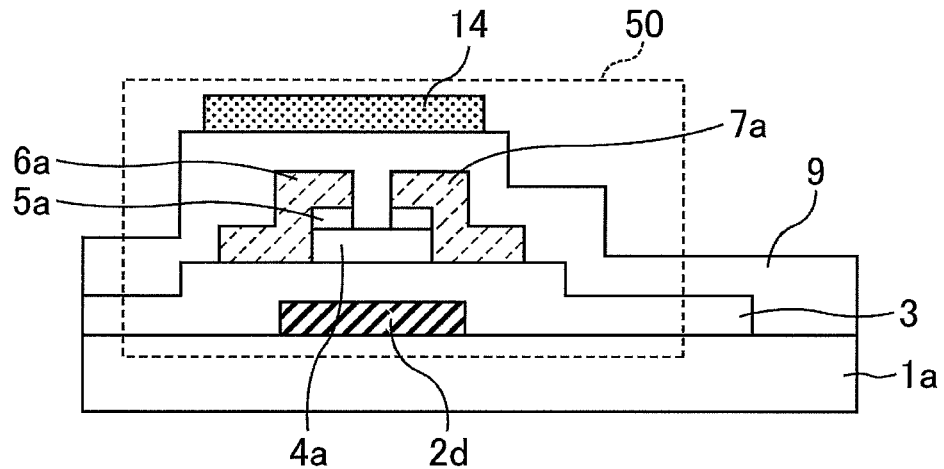
FIG. 17 is a schematic cross-sectional view of a sensor TFT 50 that is used in a double-gate sensor according to Embodiment 3.

The double-gate sensor according to the present embodiment will now be described using FIGS. 17 and 18. FIG. 17 is a schematic cross-sectional view of a sensor TFT 50 that is used in the double-gate sensor according to the present embodiment.

The sensor TFT 50 includes a gate electrode 2d, an insulating film 3 that functions as a gate insulating film, a hydrogenated a-Si layer 4a, an n+a-Si layer 5a, an electrode layer, a passivation film 9, and a back-gate electrode 14 that are formed in layers in the stated order from the substrate 1a side. The electrode layer includes a source electrode 6a and a drain electrode 7a. The n+a-Si layer 5a is doped with a fifth group element such as phosphorus (P). That is, the sensor TFT 50 is an N-channel TFT. Thus, other than having the back-gate electrode 14 that faces the hydrogenated a-Si layer 4a on the passivation film 9, the sensor TFT 50 has the same configuration as the sensor TFT 30. Note that according to the present embodiment, the passivation film 9 also functions as a gate insulator.

Figure 18:
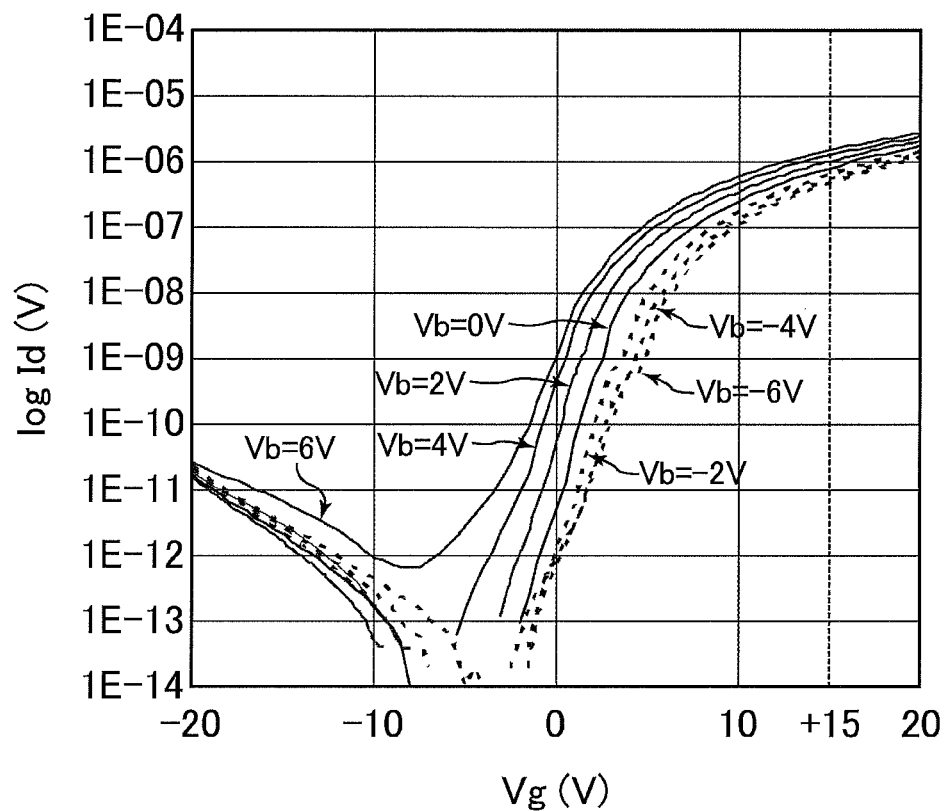
FIG. 18 illustrates Vg–Id curves with respect to the sensor TFT 50 illustrated in FIG. 17.

FIG. 18 is a graph that shows Id–Vg curves with respect to the sensor TFT 50 shown in FIG. 17, and shows Id–Vg curves when a potential (Vb) of the back-gate electrode 14 is changed from −6 V to +6 V. That is, FIG. 18 shows Vg–Id curves in a case where the sensor TFT 50 is caused to function as a double-gate sensor. Note that, a SiNx film with a thickness of 350 nm is used as the passivation film 9. Further, a voltage between the source and the drain was set to +10 V.

When the potential (Vb) of the back-gate electrode 14 is a negative potential, a threshold value of the sensor TFT 50 shifts to the positive side. That is, when Vb is a negative potential and a potential applied to the gate electrode 2d is constant (for example, +15 V), the larger that |Vb| becomes, the smaller that the current Id that flows between the drain and source is. In contrast, when Vb is a positive potential, the threshold value of the sensor TFT 50 shifts to the negative side. That is, when Vb is a positive potential and a potential applied to the gate electrode 2d is constant (for example, +15 V), the larger that Vb becomes, the larger that the current Id flowing between the drain and source is. Accordingly, when the ion sensor antenna is connected to the back-gate electrode 14, and when Vb becomes a different potential depending on an ion amount detected (captured) by the ion sensor antenna, it is possible for the double-gate sensor to measure a concentration of both positive ions and negative ions based on Id.

Figure 19:
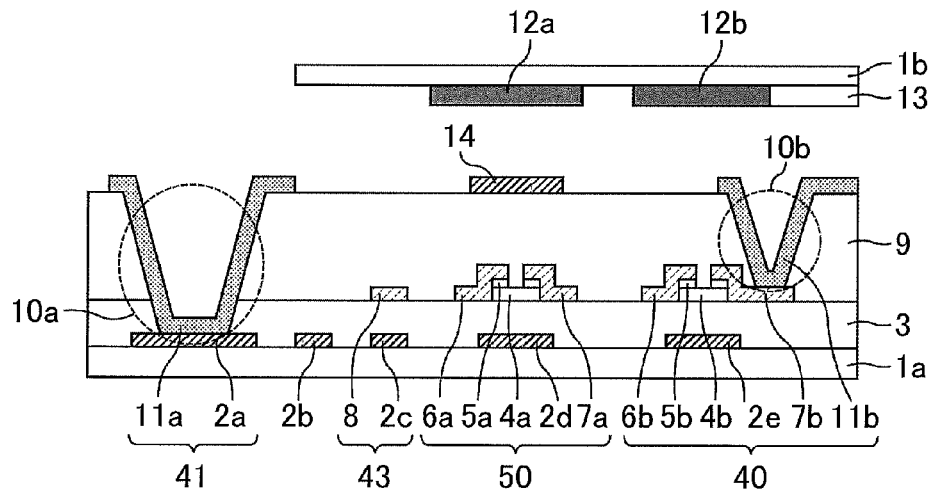
FIG. 19 is a schematic cross-sectional view illustrating a cross-section of an ion sensor and a display device according to Embodiments 3 and 4.

The structure of the ion sensor and the display device according to the present embodiment will now be described in detail using FIG. 19. FIG. 19 is a schematic cross-sectional view that shows a cross section of the ion sensor and the display device according to the present embodiment. A description of common components with respect to the display device according to Embodiment 1 is omitted here.

The back-gate electrode 14 is formed on the passivation film 9. The back-gate electrode 14 is connected to the gate electrode 2d and the antenna electrode 2a through a contact hole (not shown) that penetrates through the insulating film 3 and the passivation film 9. The back-gate electrode 14 is formed in the third conductive layer. Accordingly, it is possible to form the back-gate electrode 14 from the same material and by the same process as the transparent conductive film 11a and/or 11b.

Figure 20:
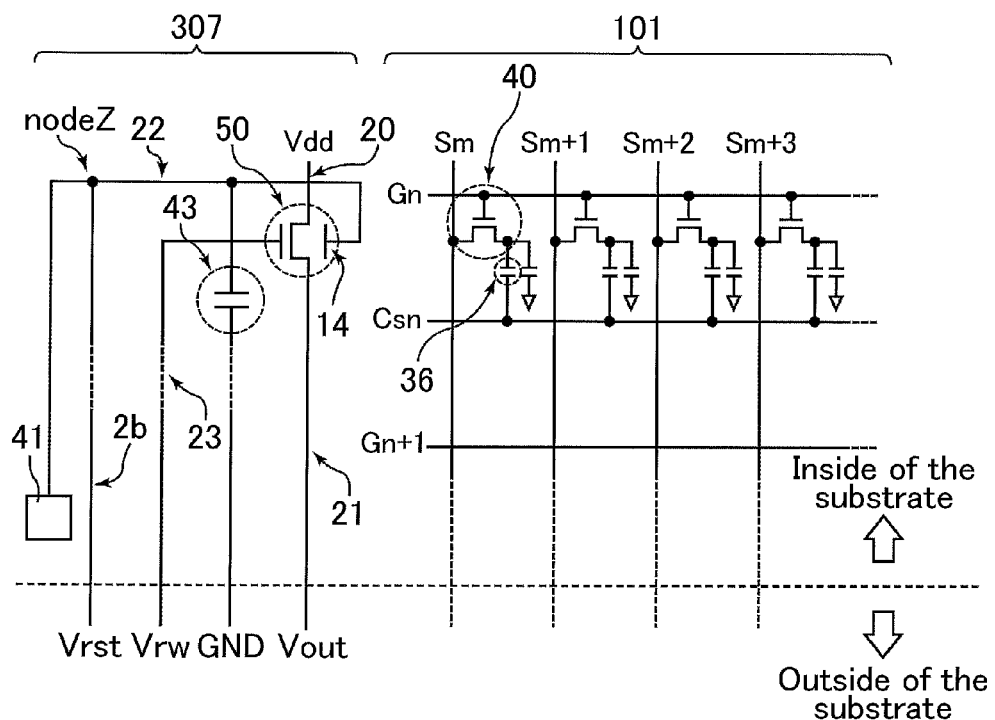
FIG. 20 is an equivalent circuit illustrating an ion sensor circuit 307 and a TFT array 101 according to Embodiments 3 and 4.

Next, the circuit configuration and operational mechanism of an ion sensor circuit 307 according to the present embodiment is described using FIG. 20. FIG. 20 is an equivalent circuit that illustrates the ion sensor circuit 307 and the TFT array 101 according to the present embodiment. The display device according to the present embodiment has the same TFT array 101 as Embodiment 1, and hence a description thereof is omitted here.

The circuit configuration of the ion sensor circuit 307 will now be described. The input line 20 is connected to the drain electrode 7a of the sensor TFT 50. A high voltage (+10 V) or a low voltage (0 V) is applied to the input line 20, and the voltage of the input line 20 is taken as Vdd. The output line 21 is connected to the source electrode 6a. The voltage of the output line 21 is taken as Vout. Further, the antenna 41 is connected through the connection line 22 to the back-gate electrode 14 of the sensor TFT 50. The reset line 2b is also connected to the connection line 22. A point of intersection (node) between the lines 22 and 2b is taken as a node-Z. The reset line 2b is a line for resetting the node-Z, that is, the voltage between the back gate of the sensor TFT 50 and the antenna 41. A high voltage (+20 V) or a low voltage (−10 V) is applied to the reset line 2b, and the voltage of the reset line 2b is taken as Vrst. In addition, a ground (GND) is connected to the connection line 22 through a storage capacitor 43. A gate control line 23 is connected to the gate electrode 2d of the sensor TFT 50. A high voltage (+20 V) or a low voltage (−10 V) is applied to the gate control line 23, and the voltage of the gate control line 23 is taken as Vrw. Similarly to Embodiment 1, a constant current circuit 25 and an analog-digital conversion circuit (ADC) 26 are connected to the output line 21.

Note that because the antenna electrode 2a, the gate electrode 2d, the reset line 2b, the storage capacitor electrode 2c, the connection line 22 and the gate control line 23 are integrally formed in the first conductive layer, the antenna 41, the gate of the sensor TFT 50, the reset line 2b, the connection line 22, the gate control line 23 and the storage capacitor 43 are connected to each other.

Figure 21:
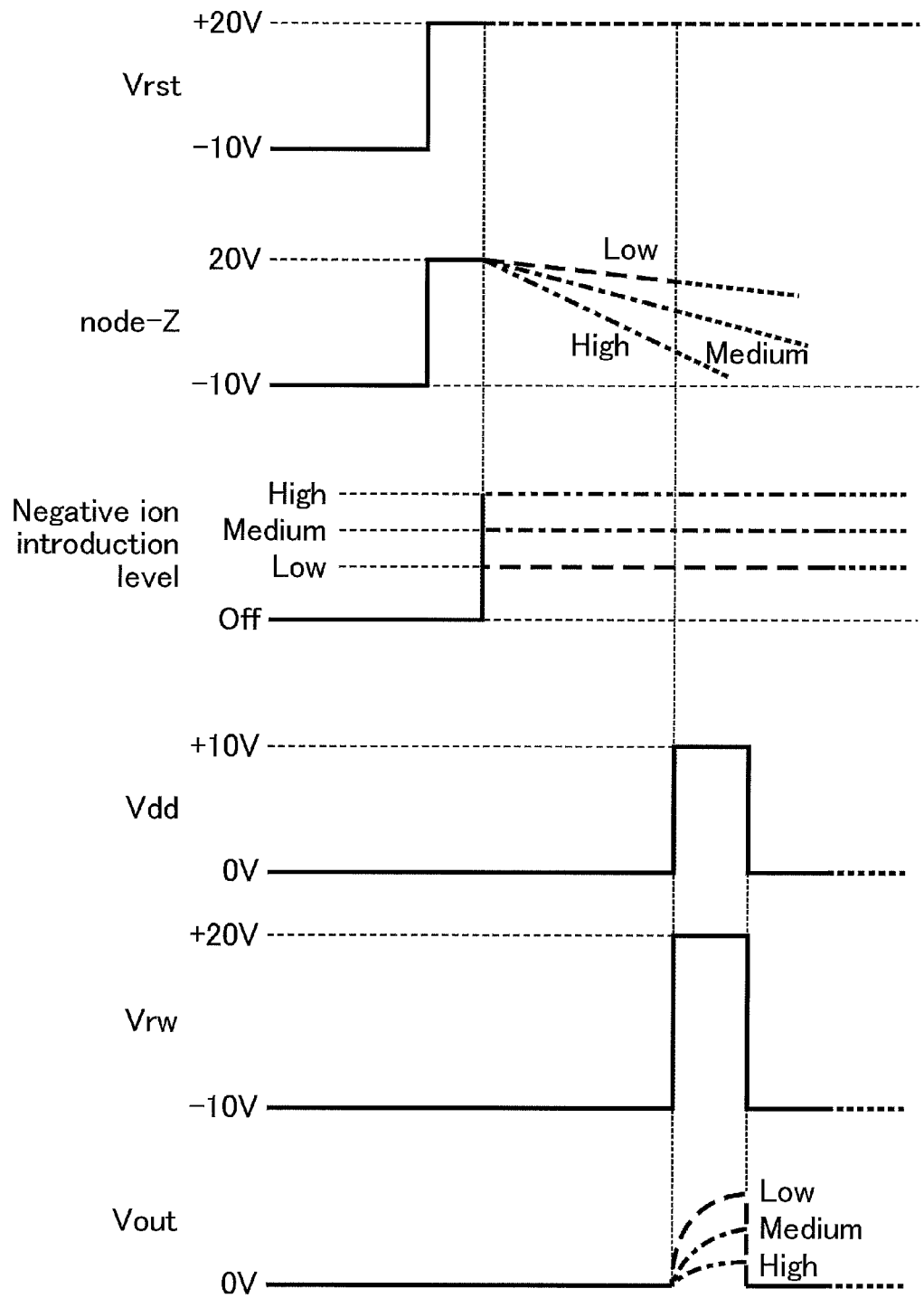
FIG. 21 is a timing chart of an ion sensor circuit according to Embodiment 3.
Figure 22:
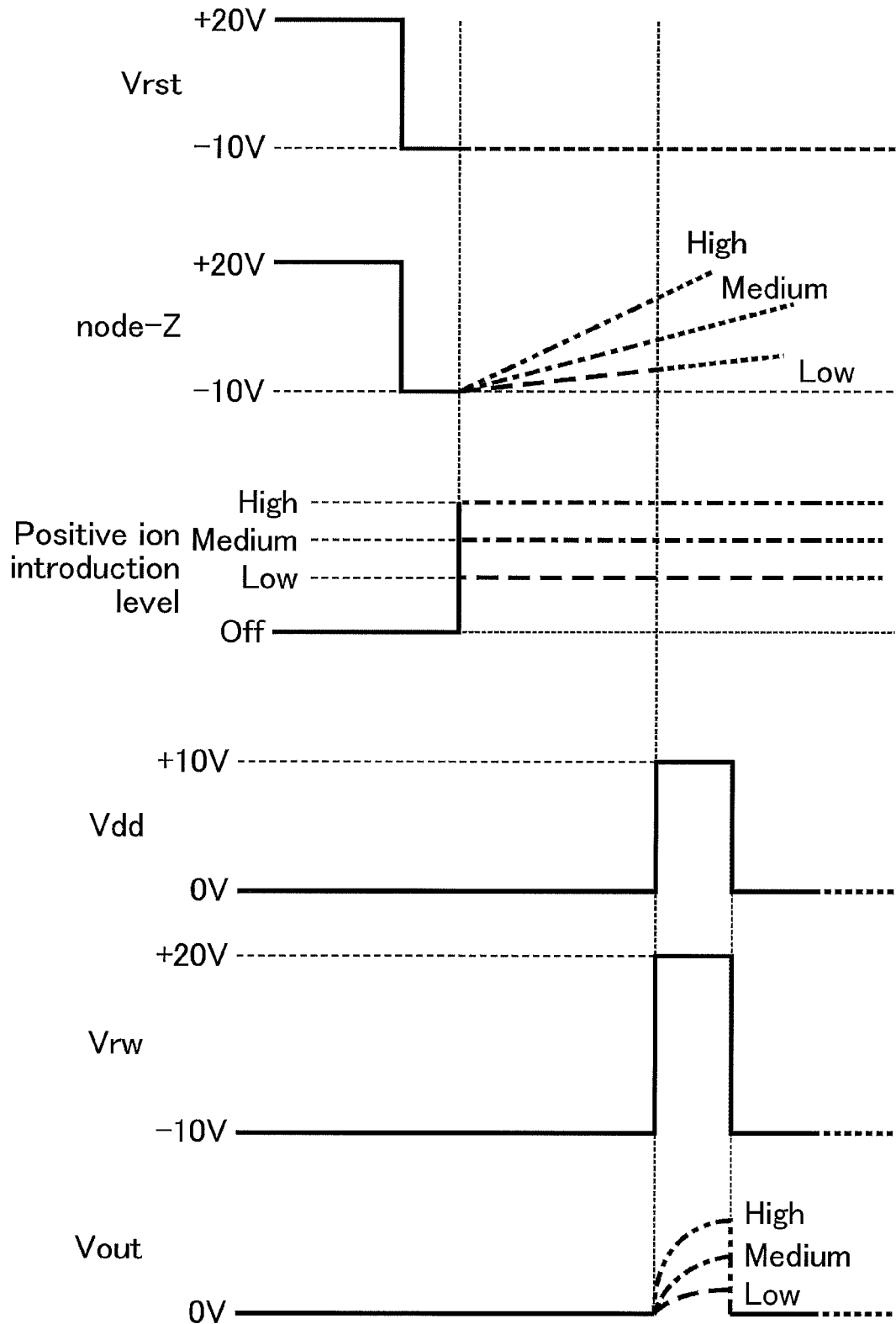
FIG. 22 is a timing chart of the ion sensor circuit according to Embodiment 3.

Next, the operational mechanism of the ion sensor circuit will be described in detail using FIGS. 21 and 22. FIG. 21 is a timing chart of the ion sensor circuit according to the present embodiment in a case of detecting negative ions. First, a case in which negative ions are detected is described.

In the initial state, Vrst is set to a low voltage (−10 V). At this time, a power supply for applying a low voltage (−10 V) to the gate electrode 2e of the pixel TFT 40 can also be used as a power supply for setting Vrst to the low voltage (−10 V). Further, in the initial state, Vdd is set to a low voltage (0 V). Before starting measurement of an ion concentration, first, a high voltage (+20 V) is applied to the reset line 2b by the reset device and the voltage of the antenna 41 (voltage of the node-Z) is reset to +20 V. At this time, a power supply for applying a high voltage (+20 V) to the gate electrode 2e of the pixel TFT 40 can also be used as a power supply for applying Vrst. After the voltage of the node-Z has been reset, the reset line 2b is held in a high impedance state by means of the reset device. Subsequently, when introduction of ions starts and negative ions are captured by the antenna 41, the voltage of the node-Z that has been reset to +20 V, that is, charged to a positive voltage, is neutralized by the negative ions and decreases. The higher the negative ion concentration is, the faster the speed at which the voltage decreases. After a predetermined time period has elapsed since introduction of ions began, a high voltage (+10 V) is temporarily applied to the input line 20. That is, a pulse voltage of +10 V is applied to the input line 20. At the same time, a high voltage (+20 V) is temporarily applied to the gate control line 23. That is, a pulse voltage of +20 V is applied to the gate control line 23. At this time, a power supply for applying a high voltage (+20 V) to the gate electrode 2e of the pixel TFT 40 can also be used as a power supply for applying Vrw. In addition, the output line 21 is connected to the constant current circuit 25. Accordingly, when a pulse voltage of +20 V is applied to the gate control line 23 at the same time as applying a pulse voltage of +10 V to the input line 20, a constant current flows in the input line 20 and the output line 21. However, a voltage Vout of the output line 21 varies in accordance with the degree of opening of the back gate of the sensor TFT 50, that is, a difference in the voltage of the node-Z. By detecting the voltage Vout with the ADC 26, it is possible to detect the negative ion concentration. The lower that the negative ion concentration is, the larger the voltage Vout becomes, and the higher that the negative ion concentration is, the smaller the voltage Vout becomes. In this connection, it is also possible to adopt a configuration in which the constant current circuit 25 is not provided, and a negative ion concentration is detected by detecting a current Id of the output line 21 that varies in accordance with a difference in the voltage of the node-Z.

Note that, according to the present embodiment, a high voltage of Vdd is not particularly limited to +10 V, and the high voltage of Vdd may be the same as a high voltage applied to the reset line 2b, that is, the same as the high voltage of +20 V that is applied to the gate electrode 2e of the pixel TFT 40. Thus, a power supply for applying the high voltage to the gate electrode 2e of the pixel TFT 40 can also be used as a power supply for applying the high voltage of Vdd.

Next, the operational mechanism of the ion sensor circuit in a case of detecting positive ions will be described in detail using FIG. 22. FIG. 22 is a timing chart of the ion sensor circuit according to the present embodiment in the case of detecting positive ions.

In the initial state, Vrst is set to a high voltage (+20 V). Further, in the initial state, Vdd is set to a low voltage (0 V). Before starting measurement of an ion concentration, first a low voltage (−10 V) is applied to the reset line 2b by means of the reset device to reset the voltage of the antenna 41 (voltage of the node-Z) to −10 V. After the voltage of the node-Z has been reset, the reset line 2b is held in a high impedance state by means of the reset device. Subsequently, when an operation to introduce ions is commenced and positive ions are captured by the antenna 41, the voltage of the node-Z that has been reset to −10 V, that is, charged to a negative voltage, is neutralized by the positive ions and increases. The higher the positive ion concentration is, the faster the speed at which the voltage increases. After a predetermined time period has elapsed since introduction of ions began, a high voltage (+10 V) is temporarily applied to the input line 20. That is, a pulse voltage of +10 V is applied to the input line 20. At the same time, a high voltage (+20 V) is temporarily applied to the gate control line 23. That is, a pulse voltage of +20 V is applied to the gate control line 23. Further, the output line 21 is connected to the constant current circuit 25. Accordingly, when a pulse voltage of +20 V is applied to the gate control line 23 at the same time as applying a pulse voltage of +10 V to the input line 20, a constant current flows in the input line 20 and the output line 21. However, a voltage Vout of the output line 21 varies in accordance with the degree of opening of the back gate of the sensor TFT 50, that is, a difference in the voltage of the node-Z. By detecting the voltage Vout with the ADC 26, it is possible to detect the positive ion concentration. The lower that the positive ion concentration is, the smaller the voltage Vout becomes, and the higher that the positive ion concentration is, the larger the voltage Vout becomes. In this connection, it is also possible to adopt a configuration in which the constant current circuit 25 is not provided, and a positive ion concentration is detected by detecting a current Id of the output line 21 that varies in accordance with a difference in the voltage of the node-Z.

As described above, according to the ion sensor of the present embodiment, it is possible to detect both positive ions and negative ions with one sensor TFT 50.

However, with respect to the sensitivity of the sensors, in general the sensitivity of the sensors of Embodiments 1 and 2 is better than the sensitivity of the sensor according to the present embodiment. The reason is described hereinafter.

First, a description will be given regarding the sensitivity of ion sensors. The potential of the antenna when starting to measure an ion concentration is taken as V0, the potential of the antenna after measuring the ion concentration over a predetermined time period t is taken as Vt, and a difference V0−Vt is taken as ΔV. Further, a drain current when starting ion concentration measurement is taken as Id,0, a drain current after the predetermined time period t elapses is taken as Id,t, and a difference Id,0−Id,t is taken as ΔId. In this case, the sensitivity is shown by ΔId/ΔV. That is, it can be said that the larger ΔId is with respect to ΔV, the higher the sensitivity is.

Figure 23:
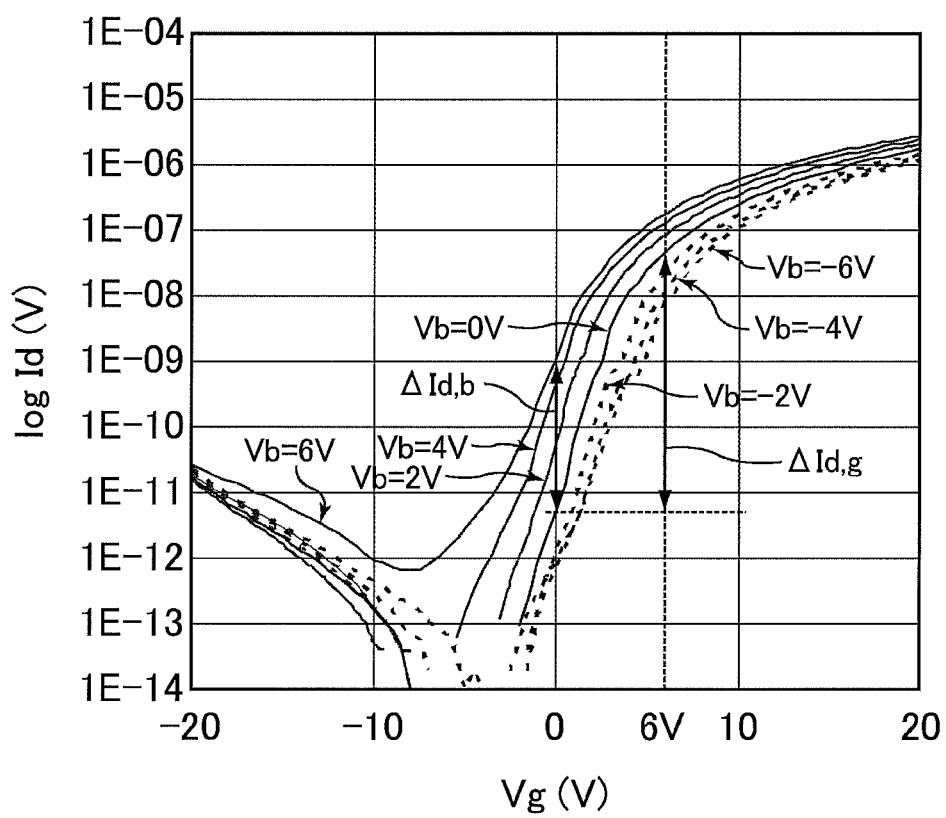
FIG. 23 illustrates Vg–Id curves with respect to a sensor TFT according to Embodiments 1 to 4.

It is generally considered that a normal gate electrode has a greater influence on the electrical conductivity of a channel than a back-gate electrode, although the level of influence also depends on the structure and design of the TFT. That is, it is considered that an electric field generated by a normal gate electrode has a stronger influence on a channel than an electric field generated by a back-gate electrode. For example, as shown in FIG. 23, a change in a drain current when a potential Vg of the gate electrode is fixed at 0 V and the potential Vb of the back-gate electrode is changed from +6 V to 0 V is taken as ΔId,b, and a change in the drain current when the back-gate electrode 14 is not provided and the potential Vg of the gate electrode is changed from +6 V to 0 V is taken as ΔId,g. In such case, ΔId,g>ΔId,b, and thus when a change in the potential of the gate electrode, and not a change in the potential of the back-gate electrode, is utilized it is found that ΔId/ΔV increases, that is, the sensitivity of the sensor increases.

Note that the reset device that is the same as in Embodiment 1 can be used as the reset device of the present embodiment when measuring a negative ion concentration. In contrast, in the case of measuring a positive ion concentration, the reset device of the present embodiment includes a MOSFET or a TFT of an opposite conductivity type to that of the reset device of Embodiment 1, and is controlled by signals of opposite polarity to Embodiment 1.

(Embodiment 4)

A display device according to Embodiment 4 has the same configuration as Embodiment 3, except for the following points. That is, although the display device according to Embodiment 3 includes an ion sensor that is capable of measuring a ion concentration in the atmosphere using the N-channel sensor TFT 50 that includes a back gate, the display device according to Embodiment 4 includes an ion sensor that is capable of measuring an ion concentration in the atmosphere using a P-channel sensor TFT 50 that includes a back gate.

More specifically, p+a-Si layers are formed instead of the n+a-Si layers 5a and 5b, and the p+a-Si layers are doped with a third group element such as boron (B). That is, according to the present embodiment, the sensor TFT 50 and the pixel TFT 40 are P-channel TFTs.

Figure 24:
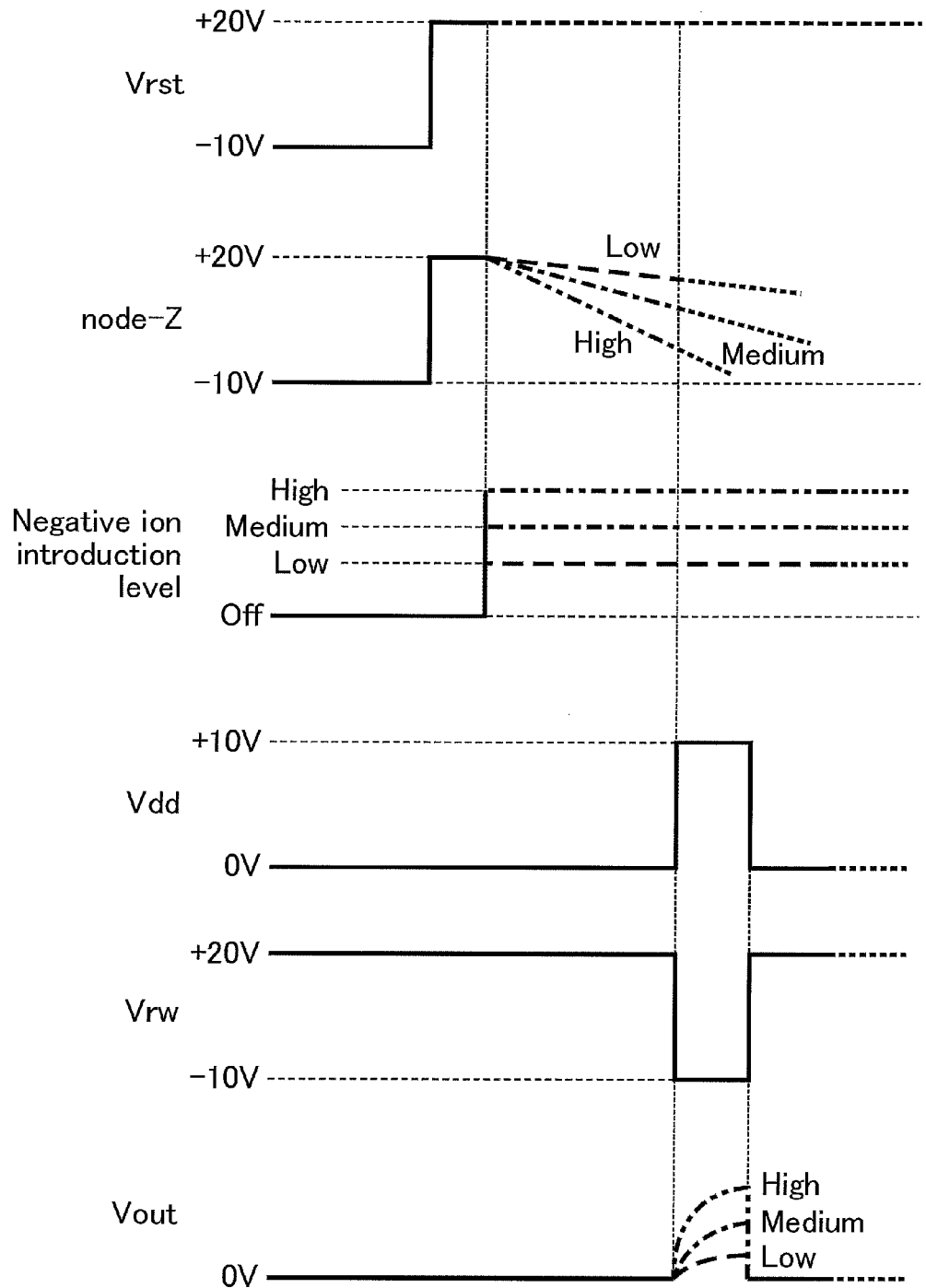
FIG. 24 is a timing chart of an ion sensor circuit according to Embodiment 4.
Figure 25:
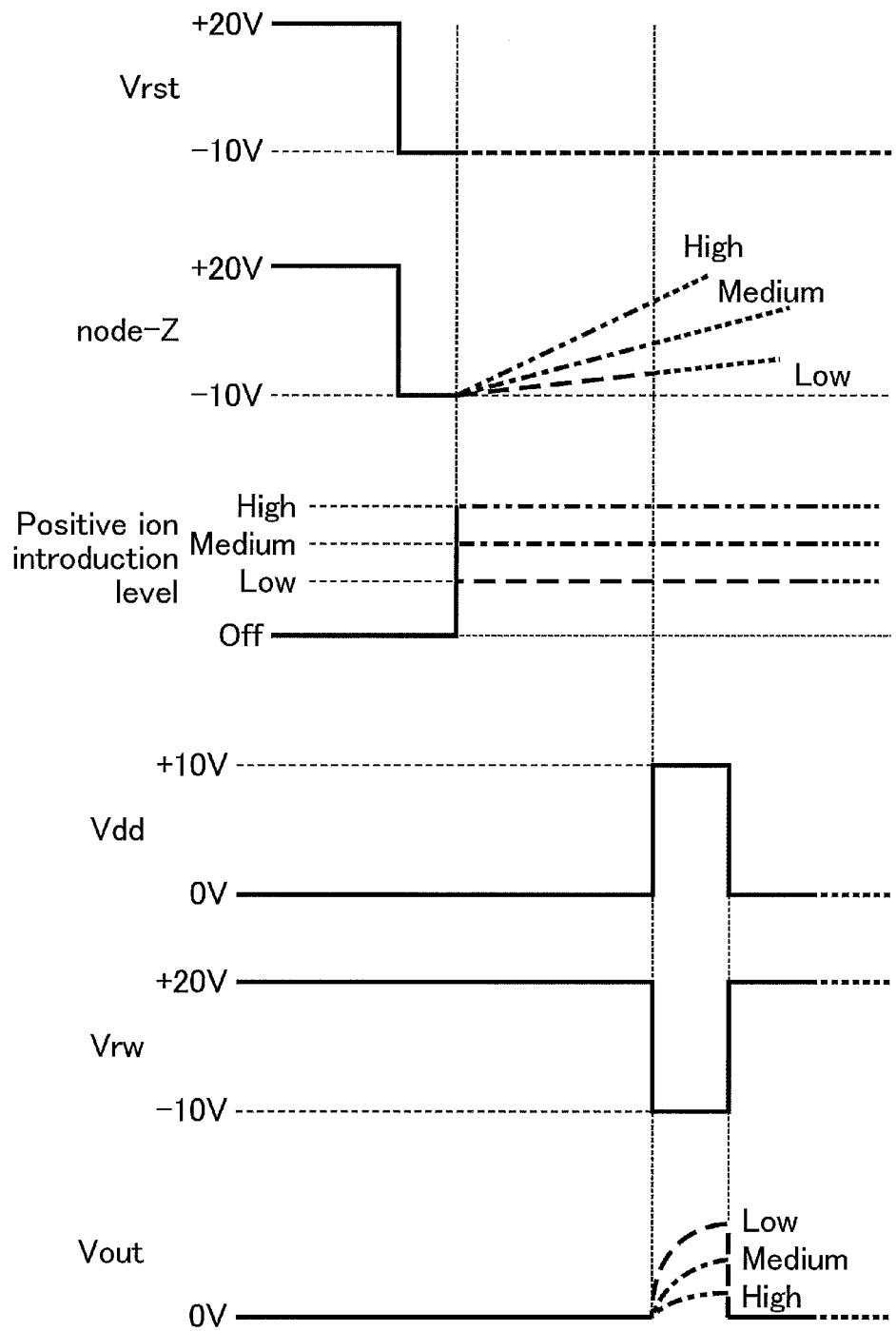
FIG. 25 is a timing chart of the ion sensor circuit according to Embodiment 4.

Next, the operational mechanism of the ion sensor circuit will be described in detail using FIGS. 24 and 25. FIG. 24 is a timing chart of the ion sensor circuit according to the present embodiment in a case of detecting negative ions. First, a case in which negative ions are detected is described.

In the initial state, Vrst is set to a low voltage (−10 V). At this time, a power supply for applying a low voltage (−10 V) to the gate electrode 2e of the pixel TFT 40 can also be used as a power supply for setting Vrst to the low voltage (−10 V). Further, in the initial state, Vdd is set to a low voltage (0 V). Before starting measurement of an ion concentration, first, a high voltage (+20 V) is applied to the reset line 2b by means of the reset device and the voltage of the antenna 41 (voltage of the node-Z) is reset to +20 V. At this time, a power supply for applying a high voltage (+20 V) to the gate electrode 2e of the pixel TFT 40 can also be used as a power supply for applying Vrst. After the voltage of the node-Z has been reset, the reset line 2b is held in a high impedance state by the reset device. Subsequently, when introduction of ions starts and negative ions are captured by the antenna 41, the voltage of the node-Z that has been reset to +20 V, that is, charged to a positive voltage, is neutralized by the negative ions and decreases. The higher the negative ion concentration is, the faster the speed at which the voltage decreases. After a predetermined time period has elapsed since introduction of ions began, a high voltage (+10 V) is temporarily applied to the input line 20. That is, a pulse voltage of +10 V is applied to the input line 20. At the same time, a low voltage (−10 V) is temporarily applied to the gate control line 23. That is, a pulse voltage of −10 V is applied to the gate control line 23. At this time, a power supply for applying a low voltage (−10 V) to the gate electrode 2e of the pixel TFT 40 can also be used as a power supply for applying Vrw. In addition, the output line 21 is connected to the constant current circuit 25. Accordingly, when a pulse voltage of −10 V is applied to the gate control line 23 at the same time as applying a pulse voltage of +10 V to the input line 20, a constant current flows in the input line 20 and the output line 21. However, a voltage Vout of the output line 21 varies in accordance with the degree of opening of the back gate of the sensor TFT 50, that is, a difference in the voltage of the node-Z. By detecting the voltage Vout with the ADC 26, it is possible to detect the negative ion concentration. The lower that the negative ion concentration is, the smaller the voltage Vout becomes, and the higher that the negative ion concentration is, the larger the voltage Vout becomes. In this connection, it is also possible to adopt a configuration in which the constant current circuit 25 is not provided, and a negative ion concentration is detected by detecting a current Id of the output line 21 that varies in accordance with a difference in the voltage of the node-Z.

Note that, according to the present embodiment, a high voltage of Vdd is not particularly limited to +10 V, and the high voltage of Vdd may be the same as a high voltage applied to the reset line 2b, that is, the same as the high voltage of +20 V that is applied to the gate electrode 2e of the pixel TFT 40. Thus, a power supply for applying the high voltage to the gate electrode 2e of the pixel TFT 40 can also be used as a power supply for applying the high voltage of Vdd.

Next, the operational mechanism of the ion sensor circuit in a case of detecting positive ions will be described in detail using FIG. 25. FIG. 25 is a timing chart of the ion sensor circuit according to the present embodiment in the case of detecting positive ions.

In the initial state, Vrst is set to a high voltage (+20 V). Further, in the initial state, Vdd is set to a low voltage (0 V). Before starting measurement of an ion concentration, first a low voltage (−10V) is applied to the reset line 2b by means of the reset device and the voltage of the antenna 41 (voltage of the node-Z) is reset to −10 V. After the voltage of the node-Z has been reset, the reset line 2b is held in a high impedance state by means of the reset device. Subsequently, when an operation to introduce ions is commenced and positive ions are captured by the antenna 41, the voltage of the node-Z that has been reset to −10V, that is, charged to a negative voltage, is neutralized by the positive ions and increases. The higher the positive ion concentration is, the faster the speed at which the voltage increases. After a predetermined time period has elapsed since introduction of ions began, a high voltage (+10 V) is temporarily applied to the input line 20. That is, a pulse voltage of +10 V is applied to the input line 20. At the same time, a low voltage (−10 V) is temporarily applied to the gate control line 23. That is, a pulse voltage of −10 V is applied to the gate control line 23. Further, the output line 21 is connected to the constant current circuit 25. Accordingly, when a pulse voltage of −10 V is applied to the gate control line 23 at the same time as applying a pulse voltage of +10V to the input line 20, a constant current flows in the input line 20 and the output line 21. However, a voltage Vout of the output line 21 varies in accordance with the degree of opening of the back gate of the sensor TFT 50, that is, a difference in the voltage of the node-Z. By detecting the voltage Vout with the ADC 26, it is possible to detect the positive ion concentration. The lower that the positive ion concentration is, the larger the voltage Vout becomes, and the higher that the positive ion concentration is, the smaller the voltage Vout becomes. In this connection, it is also possible to adopt a configuration in which the constant current circuit 25 is not provided, and a positive ion concentration is detected by detecting a current Id of the output line 21 that varies in accordance with a difference in the voltage of the node-Z.

As described above, according to the ion sensor of the present embodiment it is possible to detect both positive ions and negative ions with one sensor TFT 50.

Note that the reset device that is the same as in Embodiment 1 can be used as the reset device of the present embodiment when measuring a negative ion concentration. In contrast, in the case of measuring a positive ion concentration, the reset device of the present embodiment includes a MOSFET or a TFT of an opposite conductivity type to that of the reset device of Embodiment 1, and is controlled by signals of opposite polarity to Embodiment 1.

Hereinafter, modification examples of Embodiments 1 to 4 are described.

Although Embodiments 1 to 4 have been described using a liquid crystal display device as an example, a display device of the each embodiment may also be an FPD such as a plasma display or an organic EL display.

The constant current circuit 25 need not be provided. That is, an ion concentration may be calculated by measuring a current between the source and drain of the sensor TFT 30.

The conductivity type of a TFT formed in the ion sensor 120 and the conductivity type of a TFT formed in the display 130 may be different from each other.

A μc-Si layer, a p-Si layer, a CG-Si layer or an oxide semiconductor layer may be used instead of the hydrogenated a-Si layer. However, since μc-Si has high sensitivity to light, similarly to a-Si, it is preferable that a TFT including a μc-Si layer is shielded from light. In contrast, since p-Si, CG-Si and an oxide semiconductor have low sensitivity to light, a TFT including a p-Si layer, a CG-Si layer or an oxide semiconductor layer need not be shielded from light.

Note that although the kind of a semiconductor included in a TFT formed in the ion sensor 120 and the kind of a semiconductor of a TFT formed in the display 130 may be different from each other, from the viewpoint of simplifying the manufacturing process it is preferable that the semiconductors are of the same kind.

The kinds of TFTs formed on the substrate 1a are not limited to a bottom-gate TFT and a double-gate TFT, and the TFTs may be a top-gate TFT or a planar TFT or the like. Further, for example, in Embodiments 1 and 2, when a planar TFT is adopted as the sensor TFT 30, the antenna 41 may be formed over a channel region of the TFT 30. That is, a configuration may be adopted in which the gate electrode 2d is exposed, and the gate electrode 2d itself is caused to function as an ion sensor antenna. In addition, for example, in Embodiments 3 and 4, the antenna 41 may be formed over a channel region of the TFT 50. That is, a configuration may be adopted in which the back-gate electrode 14 is exposed, and the back-gate electrode 14 itself is caused to function as an ion sensor antenna.

Note that the kind of TFT formed in the ion sensor 120 and the kind of TFT formed in the display 130 may be different from each other.

The gate driver 103, the source driver 104 and the driving/reading circuit 105 may be made monolithic, and formed directly on the substrate 1a.

The above embodiments may be appropriately combined with each other without departing from the scope of the present invention.

EXAMPLE 1

(Display Device)

A liquid crystal display device including an ion sensor for which a detection object is negative ions in air was prepared in the same manner as Embodiment 1. More specifically, the sensor TFT 30 was an N-channel TFT of the bottom-gate type formed from hydrogenated a-Si that was configured so that the channel length (L)/channel width (W)=4 μm/60 μm. The area of the antenna 41 was 400 μm×400 μm. A capacitor with a capacitance of 1 pF was used as the node-Z storage capacitor 43.

(Driving Conditions)

Voltages of 0 V and +10 V were adopted as the low voltage and high voltage of Vdd, respectively. Voltages of −10 V and +20 V were adopted as the low voltage and high voltage of Vrst, respectively.

(Ion Generator)

The Plasmacluster Ion Generator IG-820-W manufactured by Sharp Corporation was used as an ion generator. The term "plasmacluster ions" refers to ions that are generated by applying positive and negative voltages to discharge electrodes to electrolyze airborne water molecules and oxygen molecules to thereby generate positive ions (H+) and negative ions (O−), and allowing water molecules to gather around the positive ions (H+) and negative ions (O−) to stabilize the ions.

(Measurement Details)

Variations with time in a current Id flowing through the output line and a voltage of the node-Z were measured under a temperature condition of 27° C. with respect to four kinds of air, namely, dry air, air with a low plasmacluster ion concentration (700×10³ ions/cm³), air with a medium plasmacluster ion concentration (1500×10³ ions/cm³), and air with a high plasmacluster ion concentration (2000×10³ ions/cm³).

Figure 26:
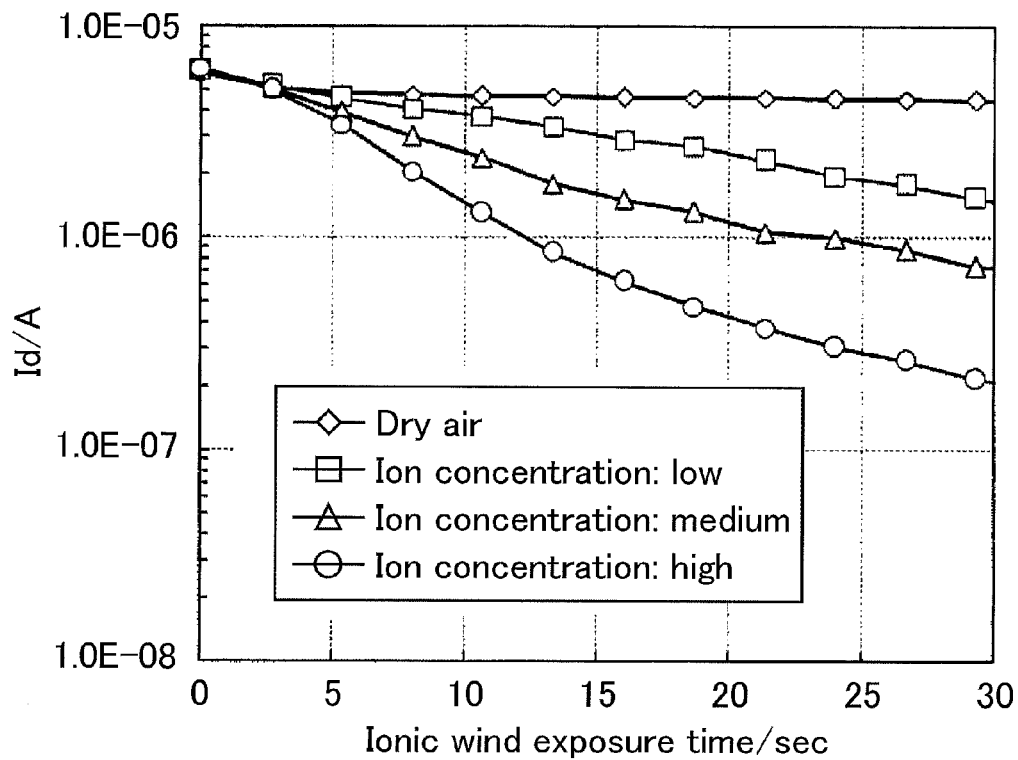
FIG. 26 is a graph that shows variations with time in Id values with respect to four kinds of air according to Example 1.

The variations with time in the Id values for the four kinds of air are shown in FIG. 26. A difference between the Id value for the high negative ion concentration and the Id value for the low negative ion concentration at 8 seconds after the start of measurement was approximately 1.5 μA.

Figure 27:
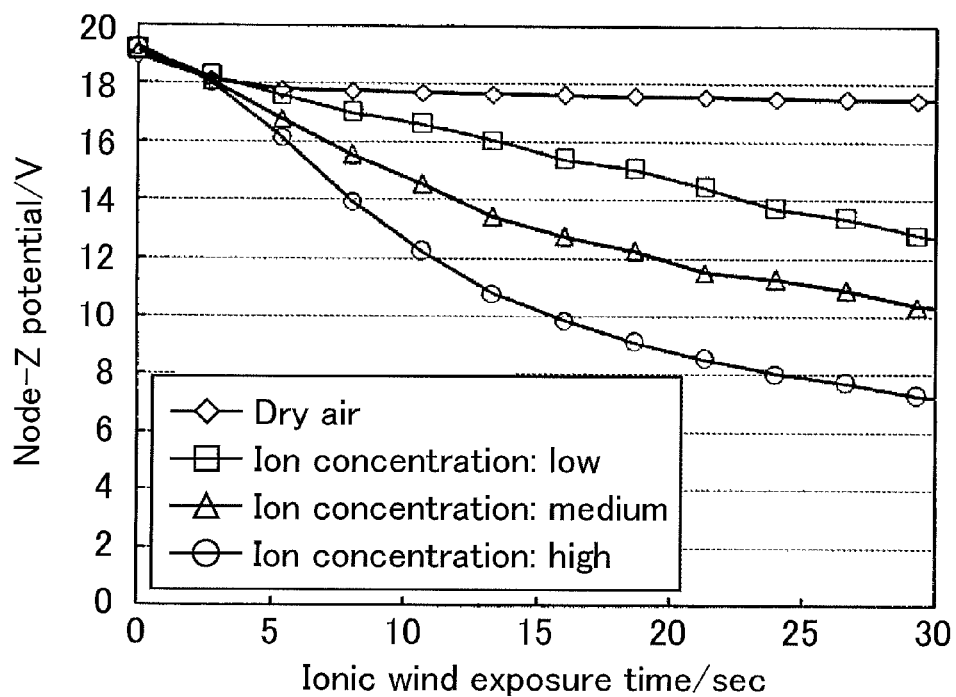
FIG. 27 is a graph that illustrates variations with time in a node-Z potential with respect to four kinds of air according to Example 1.

Variations with time in the voltage of the node-Z for the four kinds of air are shown in FIG. 27. As described in the foregoing, the higher that the negative ion concentration was, the greater the degree to which the voltage of the node-Z decreased. A difference between the voltage of the node-Z in the case of the high negative ion concentration and the voltage of the node-Z in the case of the low negative ion concentration at 8 seconds after the start of measurement was approximately 2 V.

As described above, it was established that it is possible to favorably measure a negative ion concentration in the atmosphere by means of the display device including the ion sensor according to the present example.

Further, the area occupied by the ion sensor circuit 107 of Example 1 was on the order of micrometers. In contrast, when the inventors examined the size of an ion sensor provided in a conventional ion generating apparatus, the inventors found that the ion sensor was constituted by several capacitors, several resistances, one operational amplifier, one connector, an antenna pad, a printed wiring board (PWB) and the like, and that an area occupied by the ion sensor was approximately 15 mm×45 mm, of which an area occupied by the antenna pad was approximately 10 mm×10 mm. Thus, the ion sensor circuit 107 of Example 1 was sufficiently small relative to the conventional ion sensor portion that has a comparatively large size on the order of millimeters.

Note that the ion sensor portion provided in the conventional ion generating apparatus performs from the role of an antenna portion to output of a sensor signal, and which exerts approximately the same functions as the ion sensor circuit 107 formed on the substrate 1a.

The present application claims priority to Patent Application No. 2010-128168 filed in Japan on Jun. 3, 2010 under the Paris Convention and provisions of national law in a designated State, the entire contents of which are hereby incorporated by reference.

REFERENCE SIGNS LIST 1a, 1b: Insulating substrate
2a: Ion sensor antenna electrode
2b: Reset line
2c, 8: Node-Z storage capacitor electrode
2d, 2e: Gate electrode
3: Insulating film
4a, 4b: Hydrogenated a-Si layer
5a, 5b: n+a-Si layer
6a, 6b: Source electrode
7a, 7b: Drain electrode
9: Passivation film
10a, 10b: Contact hole
11a: Transparent conductive film (first transparent conductive film)
11b: Transparent conductive film (second transparent conductive film)
12a: Light-shielding film (first light-shielding film)
12b: Light-shielding film (second light-shielding film)
13: Color filter
14: Back-gate electrode
20: Input line
21: Output line
22: Connection line
23: Gate control line
25: Constant current circuit
26: Analog-digital conversion circuit (ADC)
30, 50: Sensor TFT (first FET)
31a, 31b: Polarizer
32: Liquid crystal
36: Liquid crystal storage capacitor (Cs)
40: Pixel TFT (second FET)
41: Ion sensor antenna
42: Air ion lead-in/lead-out path
43: Node-Z storage capacitor
61n, 65n, 68n, 74n: N-channel MOSFET
61p, 68p, 74p: P-channel MOSFET
62, 64, 66, 69, 71, 73, 75, 77, 80, 82: Power supply
63a, 63b, 67, 70a, 70b, 76a, 76b, 81a, 81b: Control signal source
72n, 78n, 79n, 79p: TFT
90, 91, 92, 93, 94: Reset device
101: Display-driving TFT array
103: Gate driver (display scanning signal line-driving circuit)
104: Source driver (display image signal line-driving circuit)
105: Ion sensor driving/reading circuit
106: Arithmetic processing LSI
107, 307: Ion sensor circuit
109: Power supply circuit
110: Display device
115: Display-driving circuit
120, 125: Ion sensor
130, 135: Display

The invention claimed is:

1. A display device, comprising:
an ion sensor including:
a field effect transistor;
an ion sensor antenna; and
a reset device,
a display that includes a display-driving circuit, and
a substrate, wherein
the ion sensor antenna and the reset device are connected to a gate electrode of the field effect transistor,
the reset device is capable of controlling a potential of the gate electrode and the ion sensor antenna to a predetermined potential,
the field effect transistor, the ion sensor antenna, and at least one portion of the display-driving circuit are formed on the same main surface of the substrate,
the reset device is formed inside a semiconductor chip, and
the semiconductor chip is mounted on the substrate.

2. The ion sensor according to claim 1,
wherein the reset device includes a switching element, and after applying a predetermined voltage to the gate electrode and the ion sensor antenna, the reset device places the gate electrode and the ion sensor antenna in a high impedance state.

3. The ion sensor according to claim 1, further comprising a capacitor,
wherein
one terminal of the capacitor is connected to the gate electrode and the ion sensor antenna, and
the other terminal of the capacitor is set to a predetermined potential.

4. The ion sensor according to claim 1,
wherein the field effect transistor includes amorphous silicon or microcrystalline silicon.

5. The ion sensor according to claim 1,
wherein the field effect transistor does not include a gate electrode other than the gate electrode.

6. The ion sensor according to claim 1,
wherein the gate electrode is a first gate electrode, and the field effect transistor further includes a second gate electrode.

7. The display device according to claim 1,
wherein at least one portion of the ion sensor and at least one portion of the display-driving circuit are connected to a common power supply.

* * * * *